(12) United States Patent
Lee

(10) Patent No.: US 11,147,448 B2
(45) Date of Patent: Oct. 19, 2021

(54) HEAD MOUNTED DISPLAY DEVICE FOR EYE EXAMINATION AND METHOD FOR OPHTHALMIC EXAMINATION USING THEREFOR

(71) Applicant: M2S CO., LTD, Seongnam-si (KR)

(72) Inventor: Taehwi Lee, Seongnam-Si (KR)

(73) Assignee: M2S CO.,LTD, Seongnam-Si (KR)

( * ) Notice: Subject to any disclaimer, the term of this patent is extended or adjusted under 35 U.S.C. 154(b) by 0 days.

(21) Appl. No.: 17/273,653

(22) PCT Filed: Jul. 24, 2019

(86) PCT No.: PCT/KR2019/009156
§ 371 (c)(1),
(2) Date: Mar. 4, 2021

(87) PCT Pub. No.: WO2020/050496
PCT Pub. Date: Mar. 12, 2020

(65) Prior Publication Data
US 2021/0244271 A1 Aug. 12, 2021

(30) Foreign Application Priority Data

Sep. 4, 2018 (KR) .......... 10-2018-0105160
Sep. 4, 2018 (KR) .......... 10-2018-0105193

(51) Int. Cl.
*A61B 3/11* (2006.01)
*A61B 3/113* (2006.01)
(Continued)

(52) U.S. Cl.
CPC .......... *A61B 3/113* (2013.01); *G02B 27/0149* (2013.01); *G02B 27/0172* (2013.01);
(Continued)

(58) Field of Classification Search
CPC .. A61B 3/12; A61B 3/113; A61B 3/14; G02B 27/0149; G02B 27/0172;
(Continued)

(56) References Cited

U.S. PATENT DOCUMENTS

2015/0219902 A1\* 8/2015 Kim .................. G02B 27/0179
345/8

FOREIGN PATENT DOCUMENTS

JP 2007061507 A 3/2007
JP 2017511041 A 4/2017
(Continued)

OTHER PUBLICATIONS

International Search Report of PCT/KR2019/009156, dated Oct. 25, 2019, English translation.

*Primary Examiner* — Hung X Dang
(74) *Attorney, Agent, or Firm* — STIP Law Group, LLC

(57) ABSTRACT

An ophthalmic examination method using VR according to an embodiment of the present disclosure includes: providing an ophthalmic examination setting interface inputting a user setting for the ophthalmic examination; selecting and progressing a first ophthalmic examination in accordance with the ophthalmic examination setting interface; controlling a head mounted display to output a VR image for the first ophthalmic examination; acquiring examination data according to the VR image from the head mounted display; and outputting an ophthalmic examination progress image for an examiner for the first ophthalmic examination. As described above, since a head mounted display device for an eye examination of the present disclosure can perform various ophthalmic examinations digitally, there is an effect that it is possible to accurately and quickly determine ophthalmic examinations.

8 Claims, 18 Drawing Sheets

(51) Int. Cl.
 *G02B 27/01* (2006.01)
 *G06F 3/01* (2006.01)
 *A61B 3/14* (2006.01)

(52) U.S. Cl.
 CPC ............... *G06F 3/013* (2013.01); *A61B 3/14* (2013.01); *G02B 2027/0169* (2013.01)

(58) Field of Classification Search
 CPC ............................. G02B 27/01; G02B 27/22; G02B 2027/0169; G02F 3/013; G02F 3/011; G02F 19/006
 USPC ............... 351/206, 205, 200, 246; 345/7, 8; 359/477
 See application file for complete search history.

(56) References Cited

FOREIGN PATENT DOCUMENTS

| KR | 20140045291 A | 4/2014 |
| KR | 20150009852 A | 1/2015 |
| KR | 101704442 B1 | 2/2017 |
| KR | 20170048072 A | 5/2017 |
| KR | 20180083069 A | 7/2018 |

\* cited by examiner

[FIG. 1]
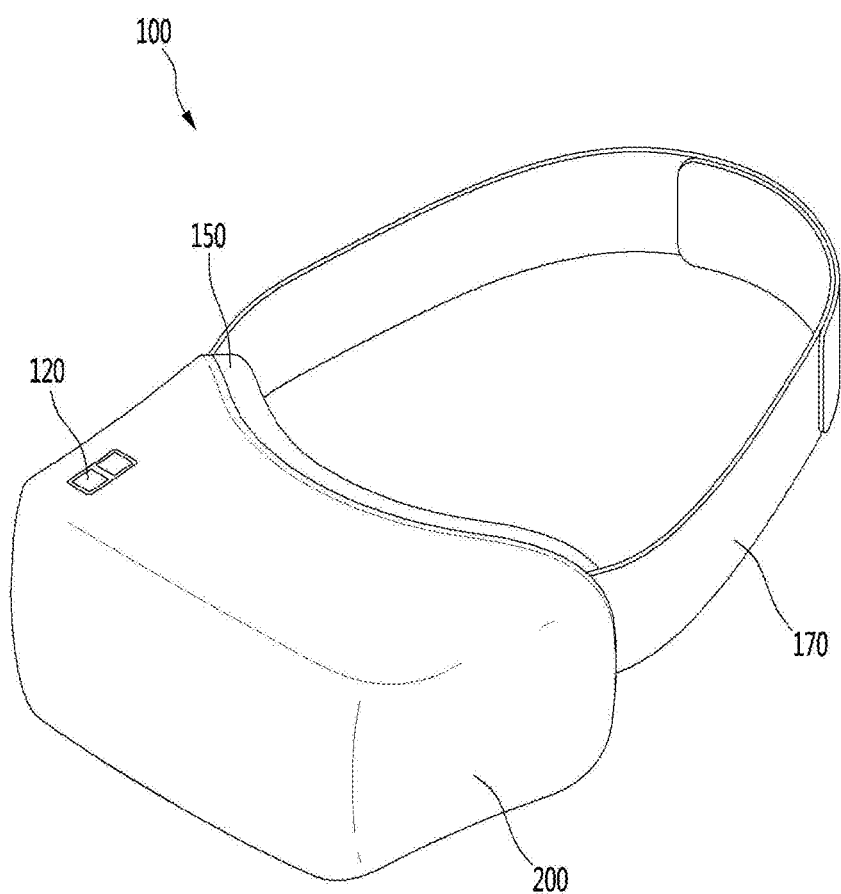

[FIG. 2]
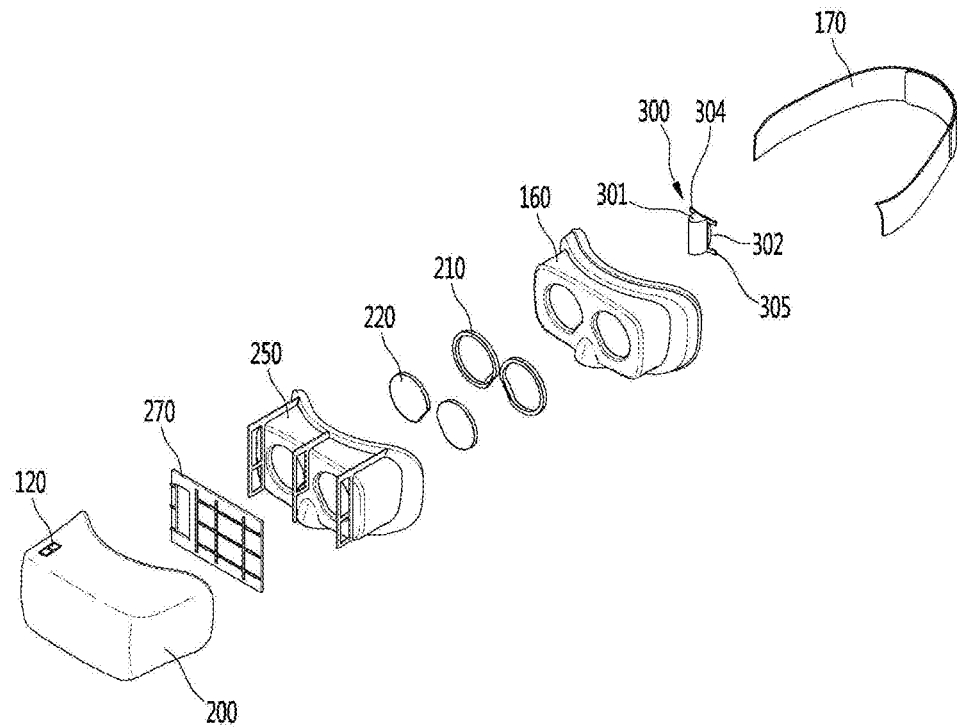
[FIG. 3]
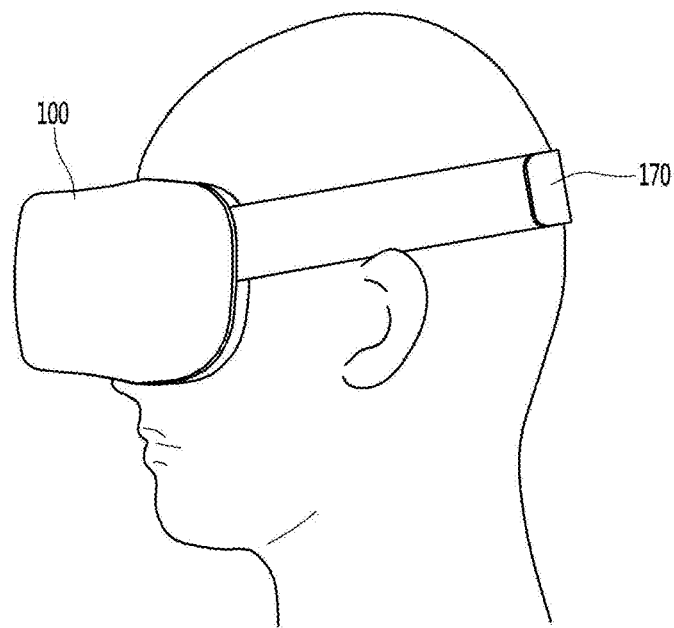

[FIG. 4]
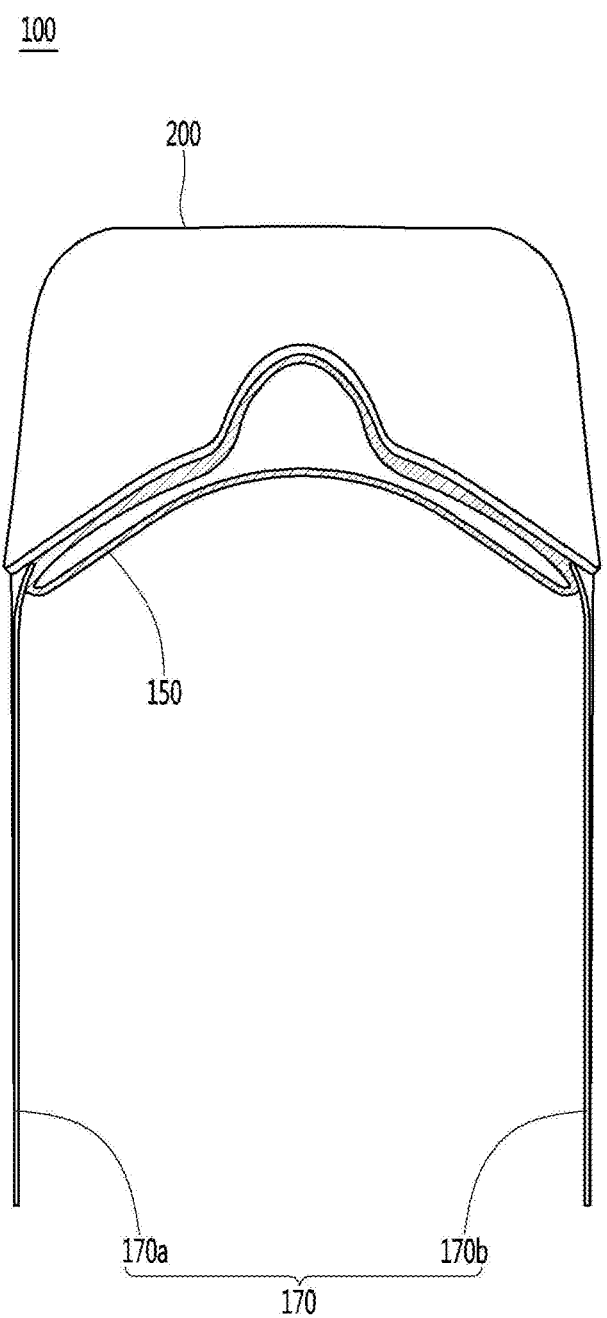

[FIG. 5]
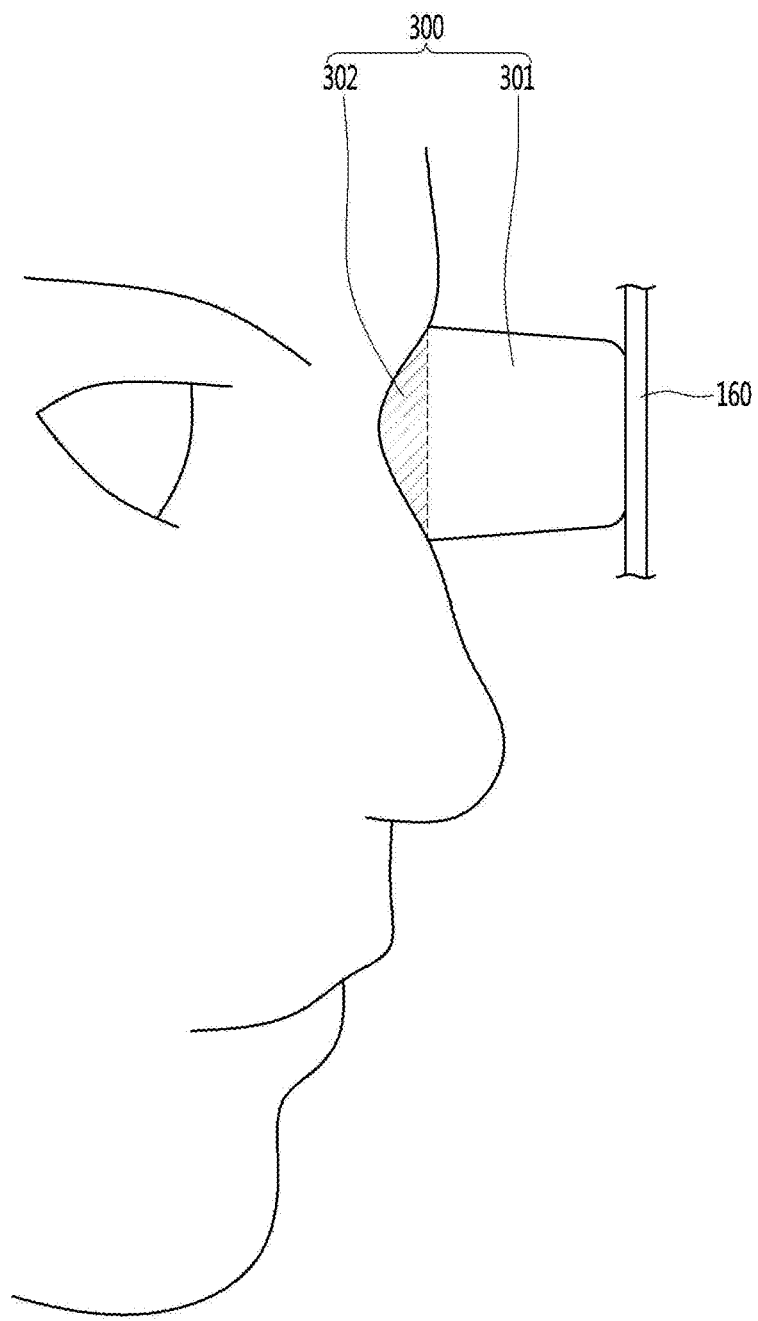

[FIG. 6]
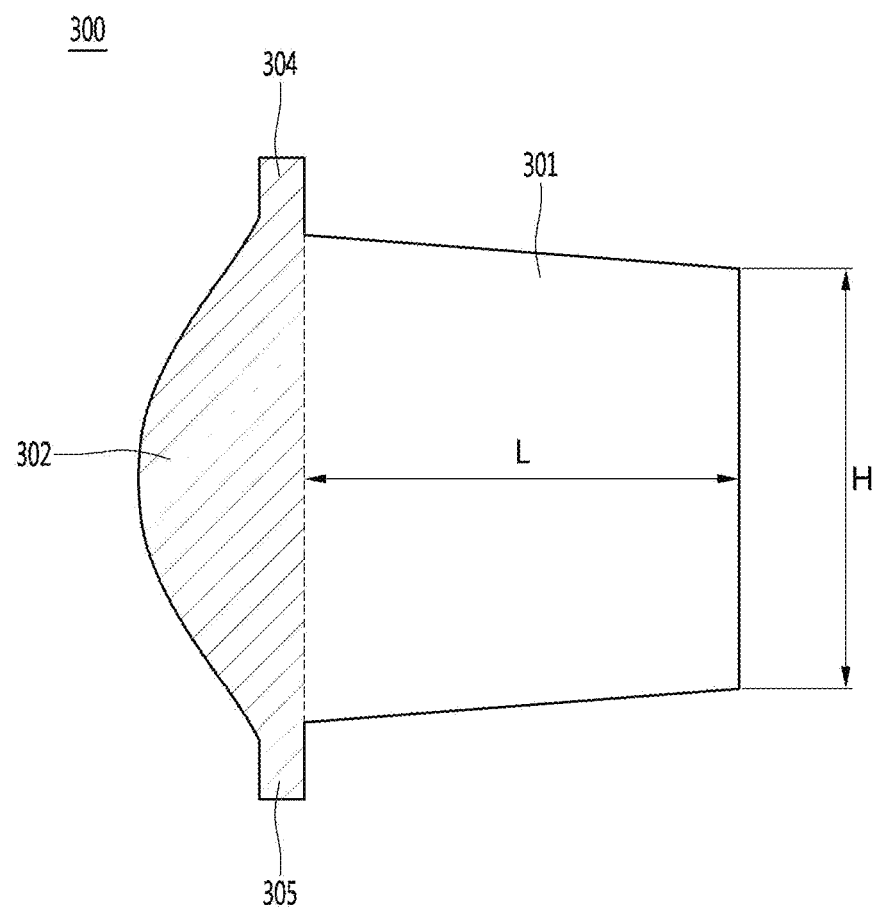

[FIG. 7]
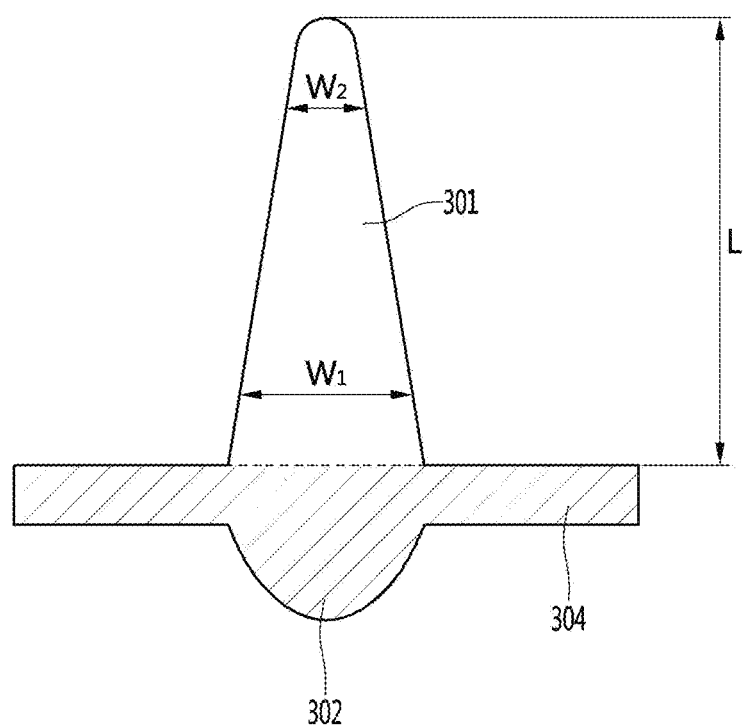

[FIG. 8]
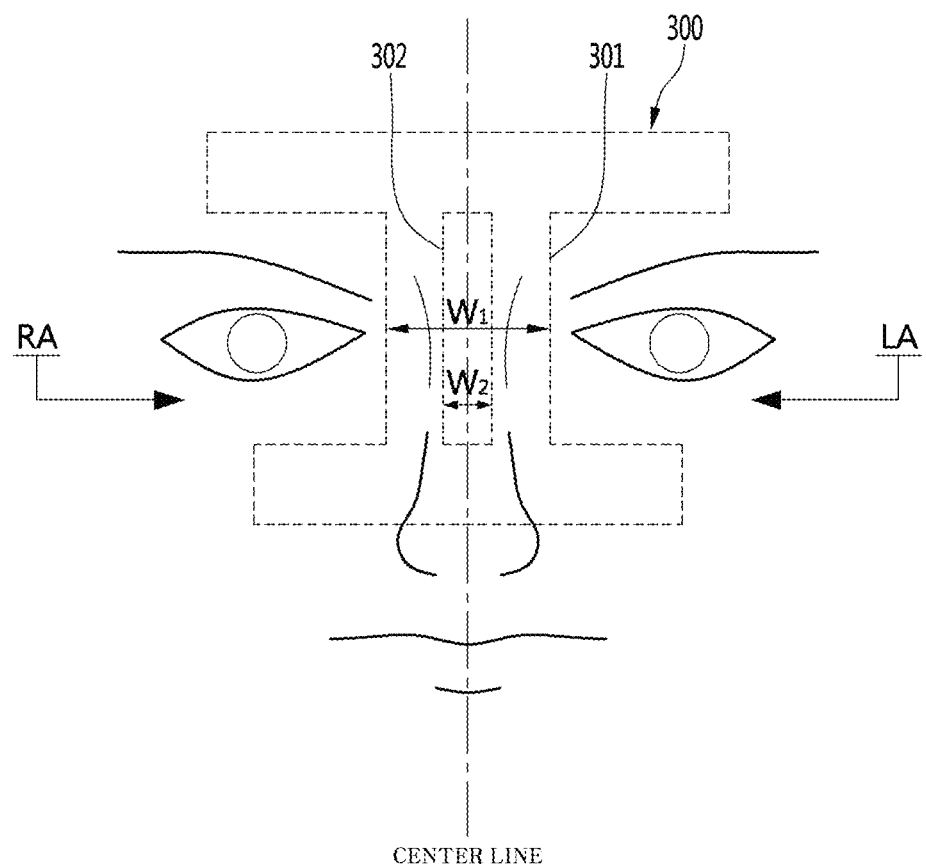

[FIG. 9]
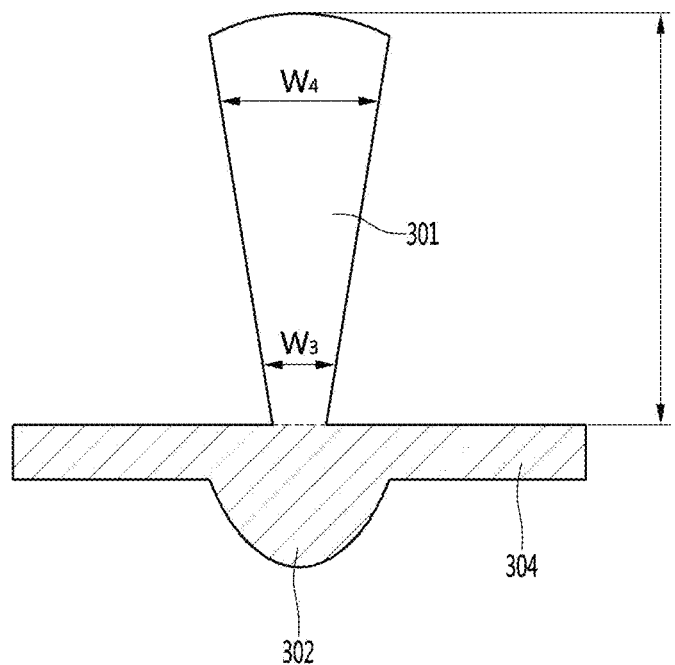
[FIG. 10]
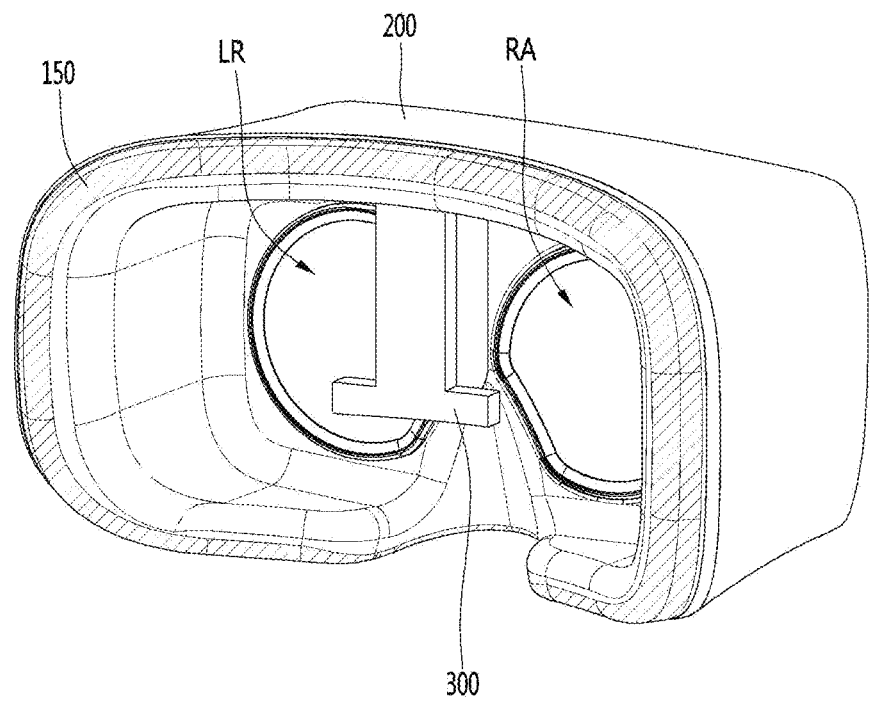

[FIG. 11]
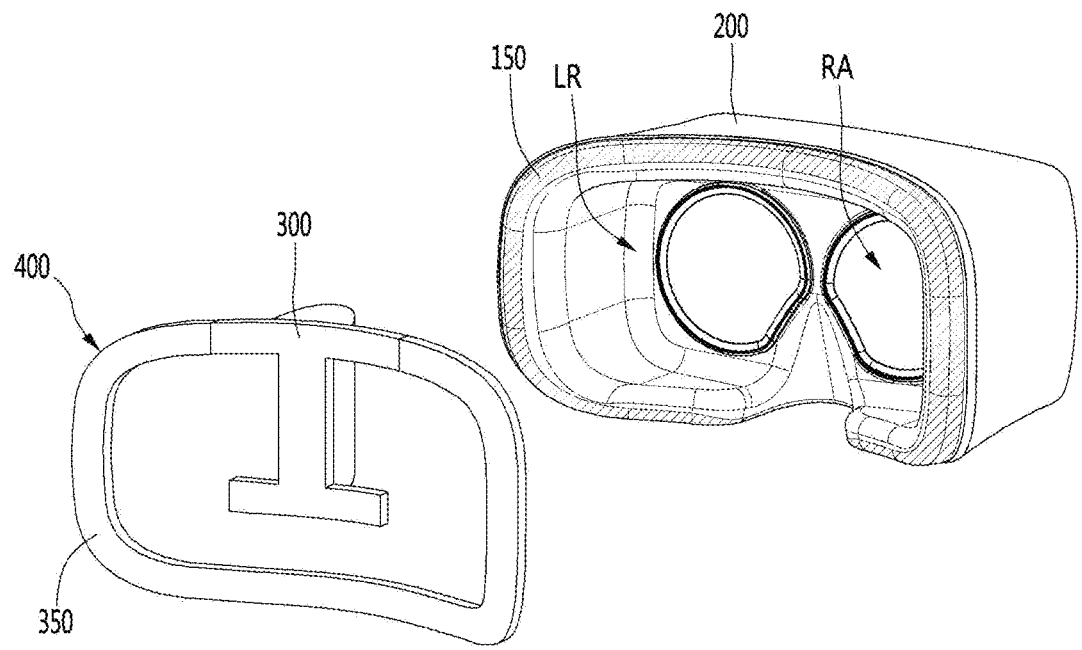
[FIG. 12]
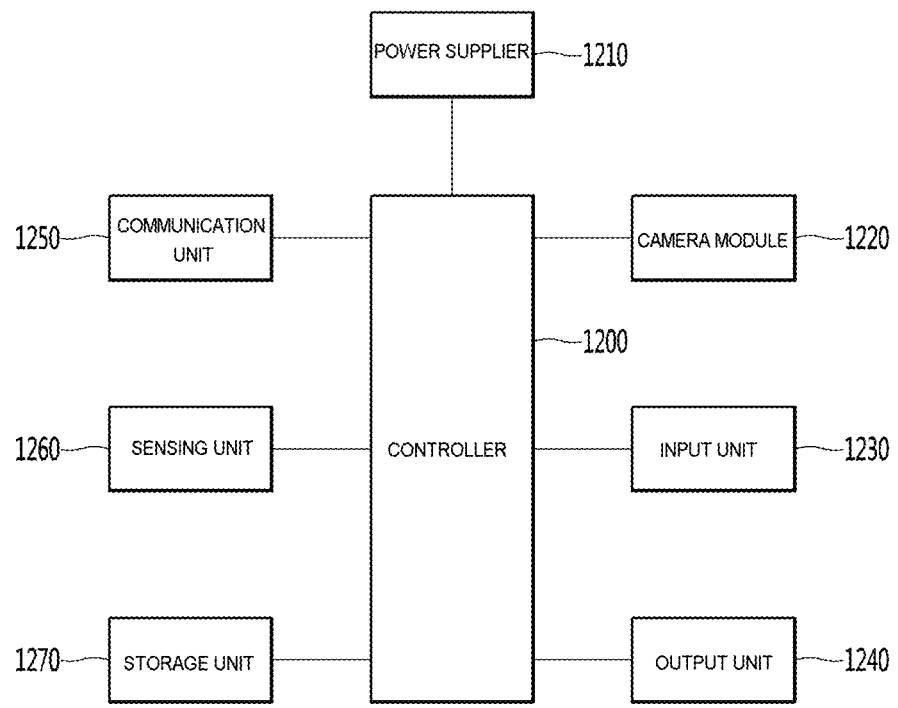

[FIG. 13]
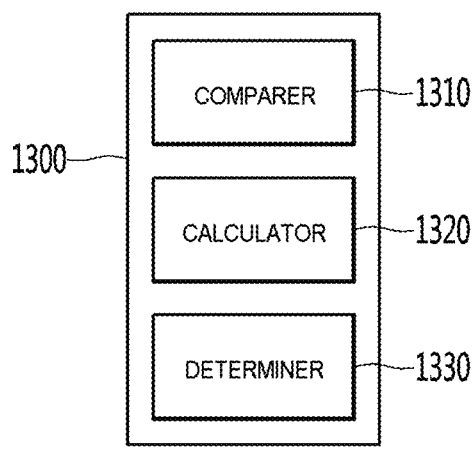
[FIG. 14]
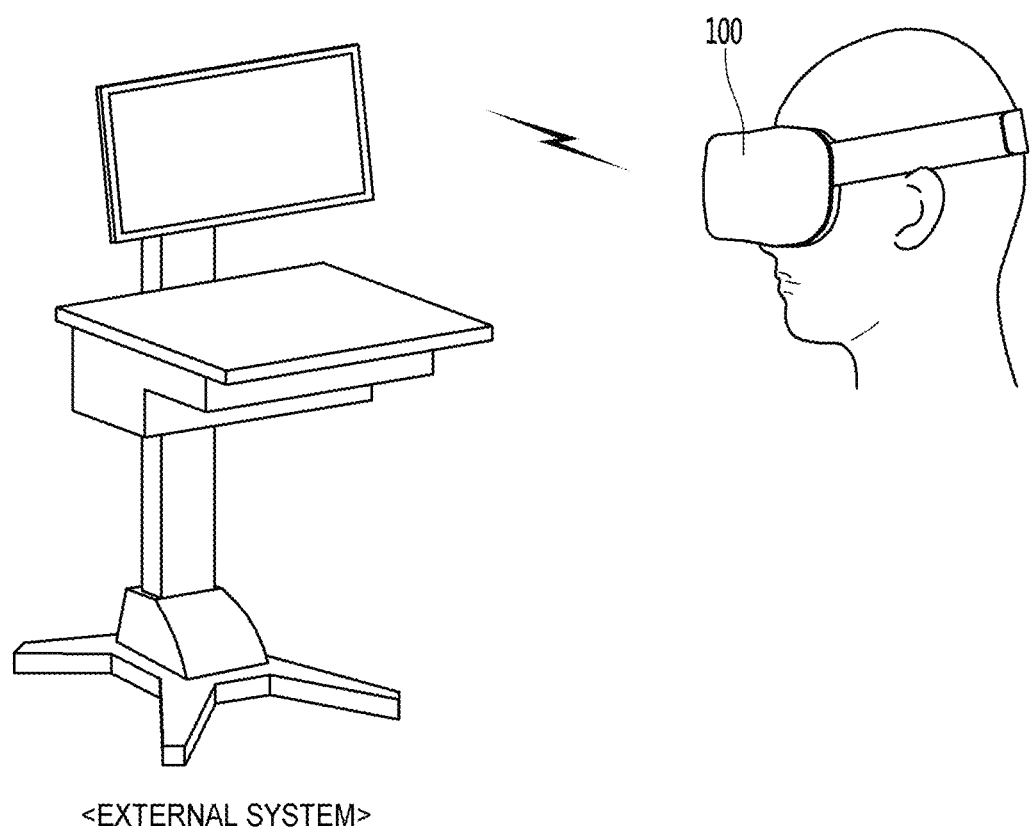
<EXTERNAL SYSTEM>

[FIG. 15]
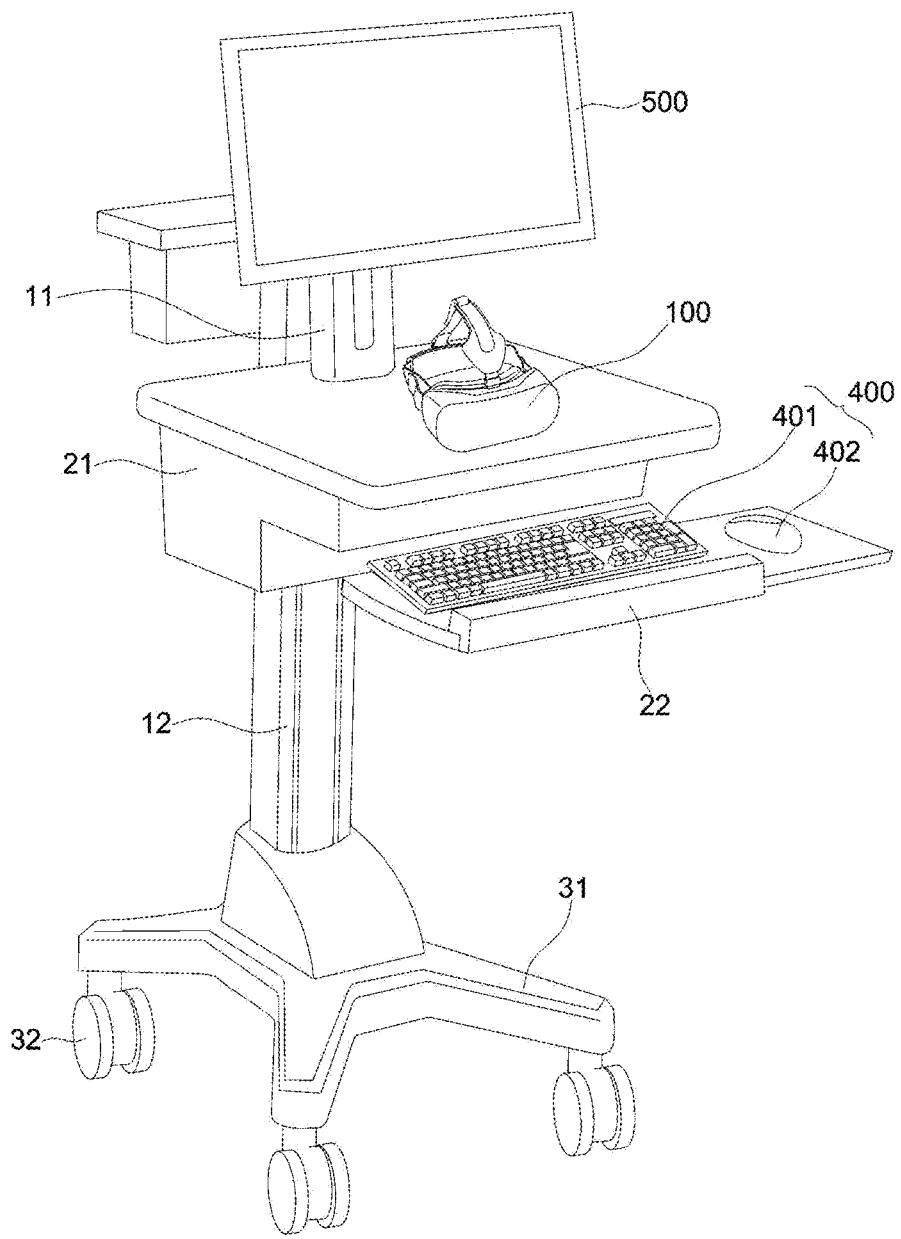

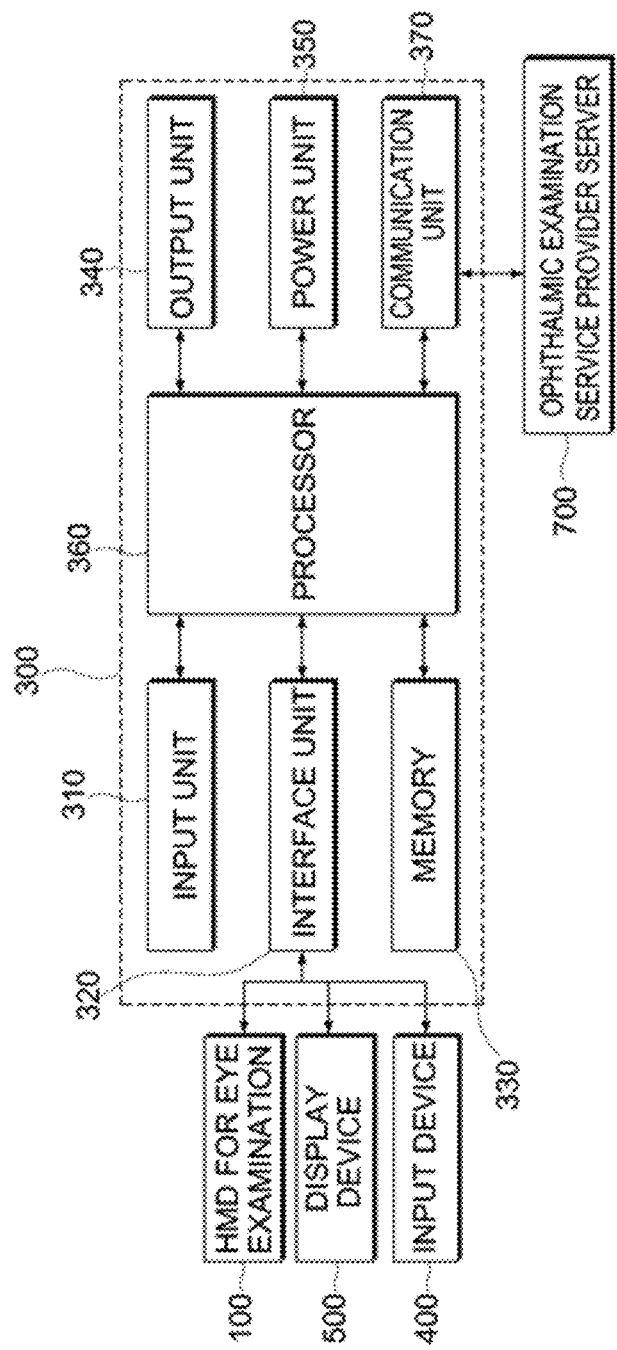
[FIG. 16]

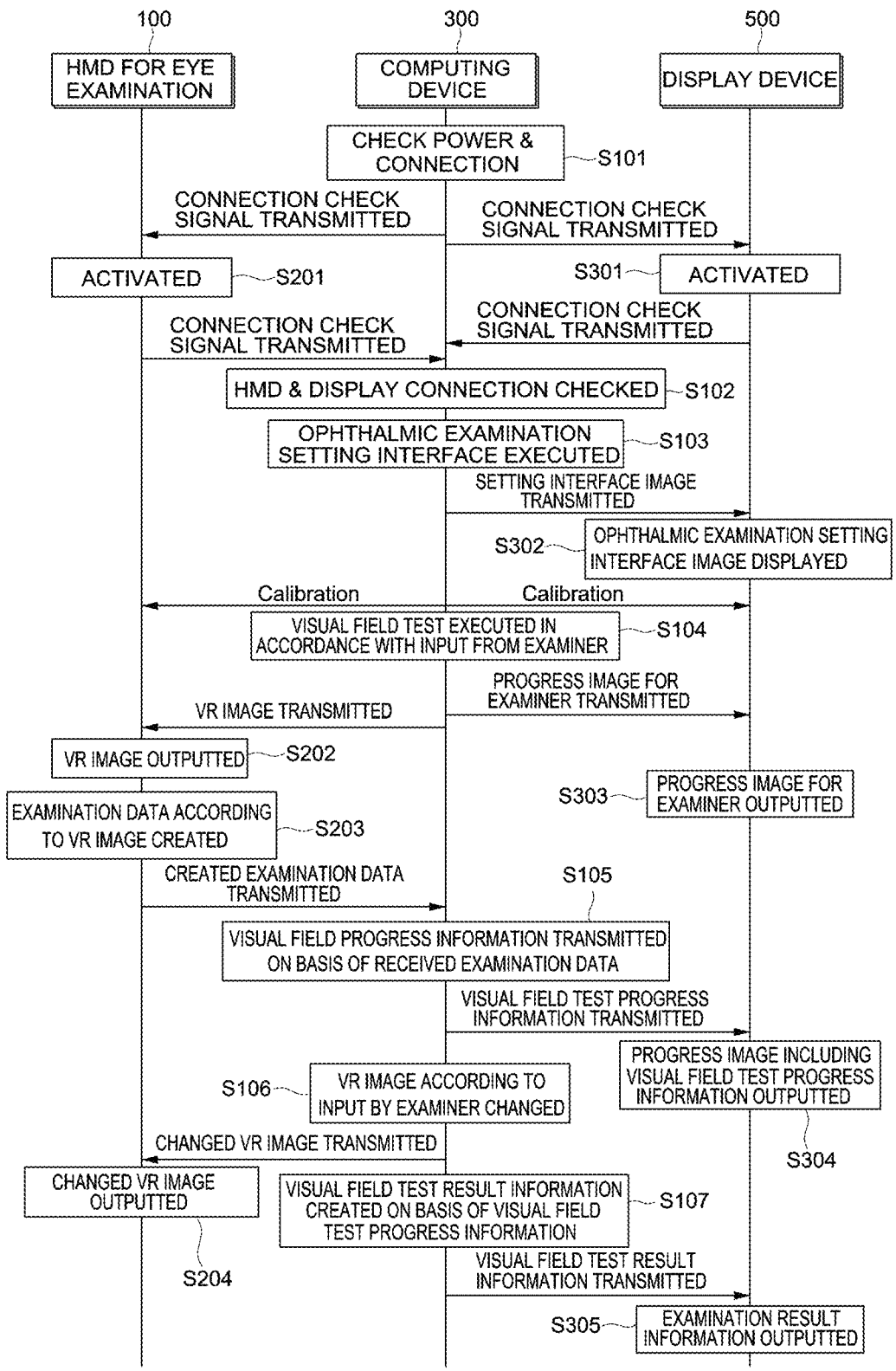
[FIG. 17]

[FIG. 18]
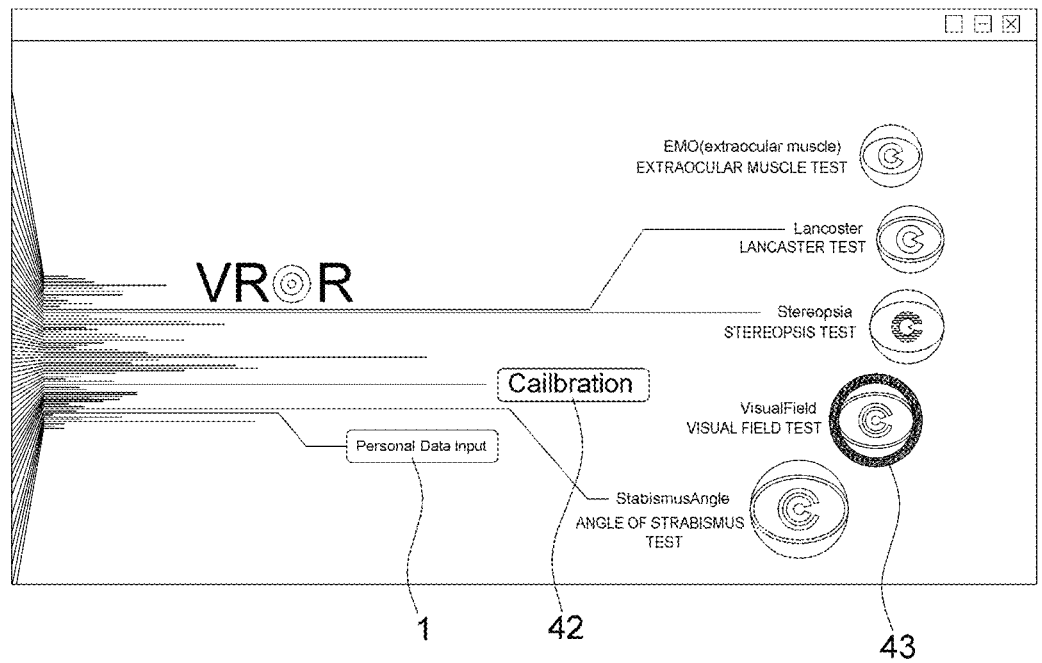
[FIG. 19A]
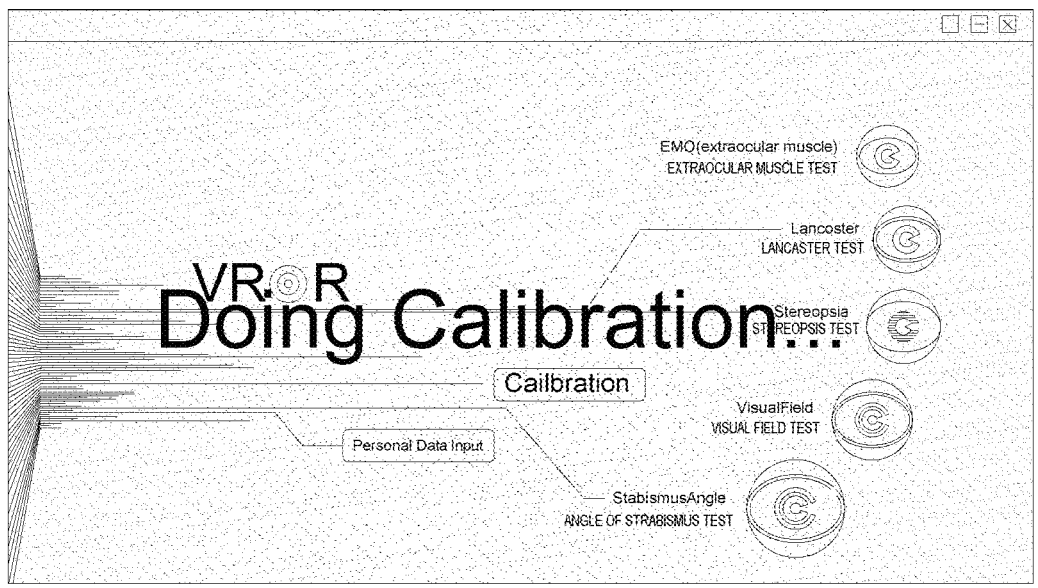

[FIG. 19B]
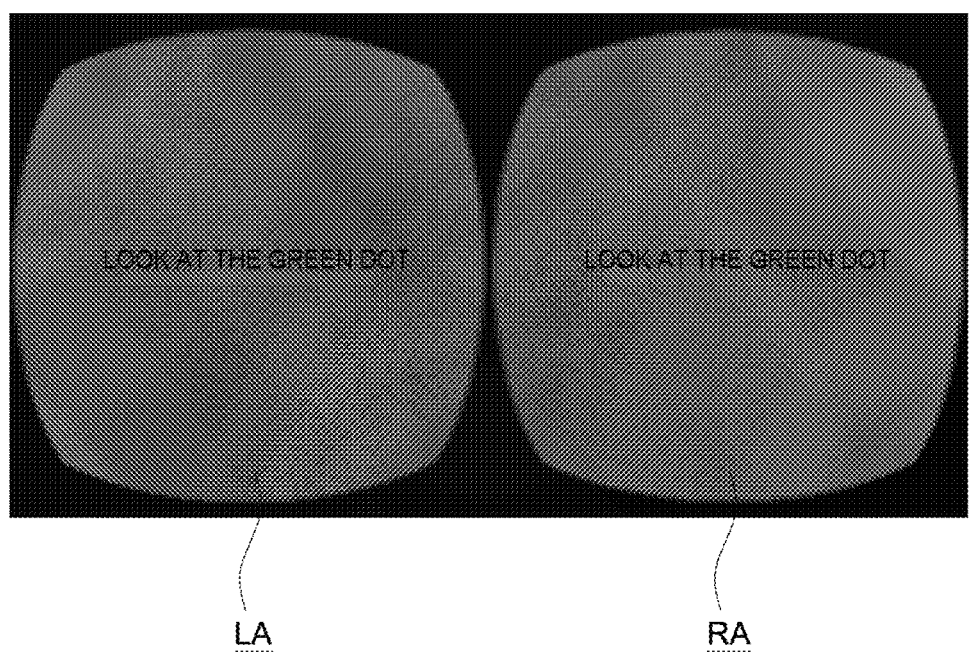

[FIG. 20]
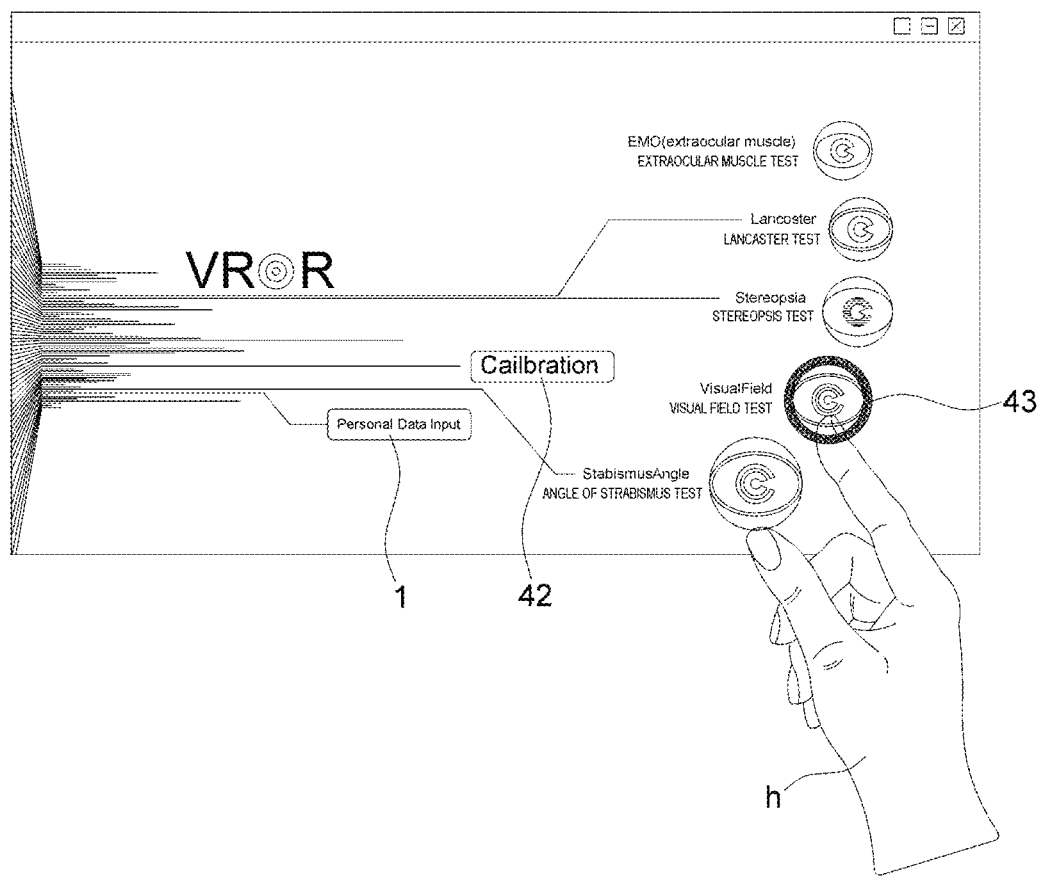
[FIG.21]
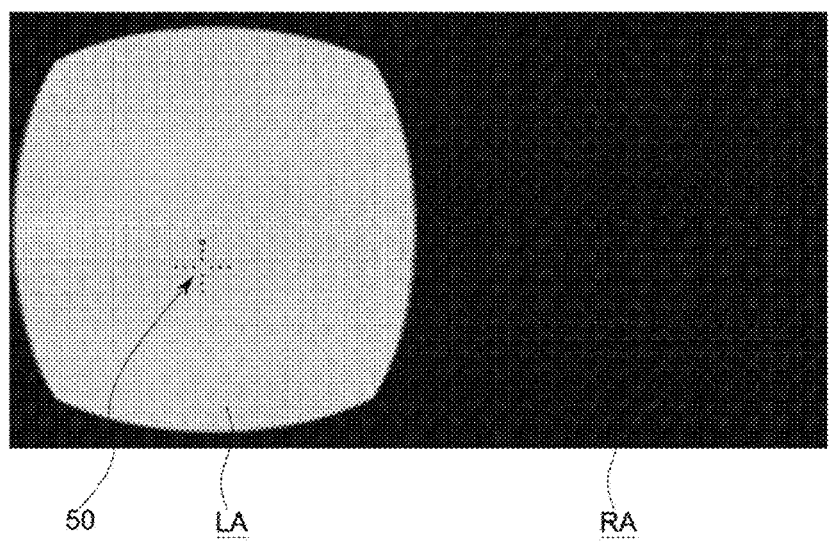

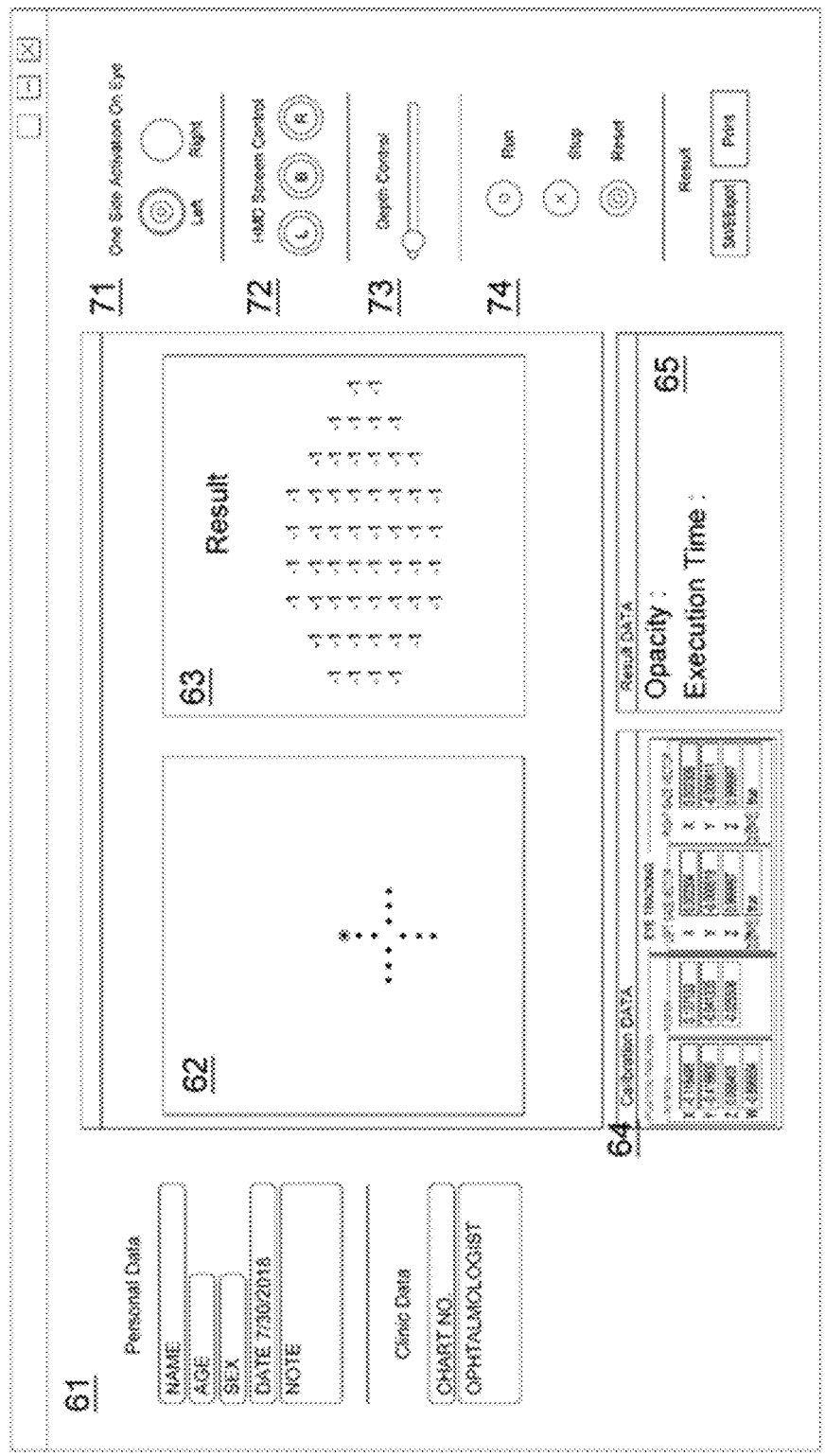

[FIG. 23]

HEAD MOUNTED DISPLAY DEVICE FOR EYE EXAMINATION AND METHOD FOR OPHTHALMIC EXAMINATION USING THEREFOR

CROSS-REFERENCE TO RELATED APPLICATIONS

This application is the U.S. National Phase under 35 U.S.C. § 371 of International Application No. PCT/KR2019/009156 filed on Jul. 24, 2019, which in turn claims the benefit of Korean Application Nos. 10-2018-0105160 filed on Sep. 4, 2018, and 10-2018-0105193 filed on Sep. 4, 2018, the disclosures of which are incorporated by reference into the present application.

BACKGROUND OF THE DISCLOSURE

Technical Field

The present disclosure relates to a head mounted display device (HMD) and, more particularly, to a head mounted display device for eye examination that can determine accurate ophthalmic diseases while quickly performing various ophthalmic examinations digitally, and an ophthalmic examination method using the device.

Related Art

Many modern people have abnormal eyesight symptoms such as nearsightedness, farsightedness, and astigmatism, depending on personal, environmental, and habitual factors. The ophthalmic diseases of humans are a concept including all problems such as a papillary problem and an eyeball movement problem in addition to abnormal eyesight.

In general, when an ophthalmic disease is suspected, a doctor or an optician performs an ophthalmic examination, and then when an ophthalmic disease is determined, a corresponding treatment is performed. For example, when there is a problem with eyesight, a doctor or an optician applies light to a crystalline lens and checks the refractive index from the reflected light, and then corrects the eyesight using glasses.

Since people show various ophthalmic disease symptoms, there are various examinations in the ophthalmic examination such as a visual field test, an angle of strabismus test, an extraocular muscle test, a stereopsis test, or a Lancaster test.

However, methods of examining ophthalmic diseases in the related art are commonly performed by examining the eye state of an examinee (eye-disease patient) using expensive eye examination equipment by an examiner (doctor or optician). Further, although eye examination equipment for eye tests of ophthalmic diseases has been substantially improved from the method that uses an eye chart in the related art, an examiner analyzes the examination information of an examinee acquired by eye examination equipment again and then determines the kinds of the ophthalmic diseases. Accordingly, there is a problem that it is difficult to quickly determine an ophthalmic disease on the basis of examination information.

Further, when an ophthalmic disease of an examinee is examined through eye examination equipment, there is a problem that the examinee is not supposed to move from the fixed position on the eye examination equipment until the examination is finished. That is, since the examination position for an ophthalmic disease of an examinee depends on eye examination equipment, the examination environment for the examinee is poor, including the case that the examinee has to take an ophthalmic examination in a stiffened state.

SUMMARY

An object of the present disclosure is to provide a head mounted display device for an eye examination that can accurately and quickly determine ophthalmic diseases by making it possible to perform various ophthalmic examinations digitally, and an ophthalmic examination method using the device.

In detail, an object of the present disclosure is to provide a head mounted display device for an eye examination that can accurately and quickly determine ophthalmic diseases by providing various ophthalmic examinations, which have been manually performed, through a virtual reality-based examination system, and an ophthalmic examination method using the device.

Another object of the present disclosure is to provide a head mounted display device for an eye examination that prevents examination errors, which may be generated by optical interference during an examination, by optically separating a left eye area and a right eye area in an area for examining an ophthalmic disease.

Another object of the present disclosure is to provide a head mounted display device for an eye examination that can examine ophthalmic diseases without specific ophthalmic examination equipment by examining an ophthalmic disease of an examinee using a VR device.

Another object of the present disclosure is to provide a head mounted display device for an eye examination that can derive objective examination data and can determine accurate ophthalmic diseases on the basis of the data by examining an ophthalmic disease of an examinee in a normalized automatic examination type.

Another object of the present disclosure is to provide a head mounted display device for an eye examination that can improve the examination environment for examinees because it is possible to wear a VR device or glasses when an examinee takes an ophthalmic examination.

Another object of the present disclosure is to provide a head mounted display device for an eye examination that can accurately and quickly determine ophthalmic diseases by making it possible to perform various ophthalmic examinations digitally.

Another object of the present disclosure is to provide an ophthalmic examination method and system using VR that can accurately and quickly determine ophthalmic diseases by providing various ophthalmic examinations, which have been manually performed, using a virtual reality-based examination system.

Another object of the present disclosure is to provide an ophthalmic examination method and system using VR that can check an examination process and can quickly and accurately proceed with an examination by outputting information related to an ophthalmic examination process in real time to an examiner.

According to the objects of the present disclosure, an ophthalmic examination of an examinee is performed through a sequential process with the examinee wearing a head mounted display, so an accurate and objective eyeball examination result can be obtained.

A head mounted display device for an eye examination of the present disclosure includes: a main body having an opening at a side; a display unit disposed in the main body and providing a VR image to an examinee through the opening; an eye examination unit examining an ophthalmic disease of an examinee together with the display unit and determining an ophthalmic disease using examination information or providing the examination information to an external system; an optical unit providing an optical lens selectively used in accordance with the kind of the ophthalmic examination of the examinee; an anti-optical interference unit separating the inside of the main body into a left eye area and a right eye area and disposed to prevent optical interference in the separated areas; and a fixing band connected to the main body, in which the anti-optical interference unit includes: an optical block optically separating a left eye area and a right eye area in the main body; and a contact-optical block preventing optical interference between the examinee and the opening of the main body in close contact with the brow and the nose ridge of the examinee.

The anti-optical interference unit further includes a first fixing portion and a second fixing portion that are attached to the brow and the nose ridge of the examinee and prevent movement of the anti-optical interference unit. The anti-optical interference unit is integrated with a housing disposed in the main body or with the main body and further includes a sanitary band corresponding to the edge of the opening area of the main body.

The width of the optical block sequentially decreases as it goes inward from the opening area of the main body or toward the opening from the inside of the main body, the optical block and the contact-optical block are integrated, the optical block and the contact-optical block are made of a material with a high light absorption ratio to prevent interference due to light reflection or light refraction, and the eye examination unit includes an optical module that can radiate or receive light for a visual field test, and a camera module that can track movement of eyeballs.

Further, an ophthalmic examination method using a head mounted display for an eye examination according to an embodiment of the present disclosure includes: providing an ophthalmic examination setting interface inputting a user setting for the ophthalmic examination; selecting and progressing a first ophthalmic examination in accordance with the ophthalmic examination setting interface; controlling a head mounted display to output a VR image for the first ophthalmic examination; acquiring examination data according to the VR image from the head mounted display; and outputting an ophthalmic examination progress image for an examiner for the first ophthalmic examination.

The providing of an ophthalmic examination setting interface may include at least one of setting a focus of an examiner in the head mounted display, and setting a first ophthalmic examination of a plurality of ophthalmic examinations.

Further, an ophthalmic examination system using VR according to an embodiment of the present disclosure includes: a display device outputting a graphic image related to an ophthalmic examination for an examiner; an input device sensing input from the examiner; and an ophthalmic examination console device controlling a head mounted display to output an examinee VR image, in which the ophthalmic examination console device outputs an ophthalmic examination setting interface image by controlling the display device, receives input by an examiner for the ophthalmic examination setting interface from the input device, determines an ophthalmic examination to be progressed in accordance with the input by the examiner, transmits a VR image for the determined ophthalmic examination to the head mounted display, receives examination data according to the VR image from the head mounted display, and outputs the received examination data in real time through the display device.

Advantageous Effects

Since a head mounted display device for an eye examination according to the present disclosure can perform various ophthalmic examinations digitally, there is an effect that it is possible to accurately and quickly determine ophthalmic examinations.

Further, since the left-eye section and the right-eye section are optically separated in the section for examining ophthalmic examinations in the head mounted display device for an eye examination according to the present disclosure, there is an effect that it is possible to prevent examination errors due to optical interference that may be generated during examinations.

Further, the head mounted display device for an eye examination according to the present disclosure implements examination of ophthalmic diseases of an examinee in a VR device type, whereby there is an effect that it is possible to examine ophthalmic diseases without specific ophthalmic examination equipment.

Further, the head mounted display device for an eye examination according to the present disclosure can derive objective examination data and can determine accurate ophthalmic diseases on the basis of the data by examining an ophthalmic disease of an examinee in a normalized automatic examination type.

Further, the head mounted display device for an eye examination according to the present disclosure can examine ophthalmic diseases in the type in which an examinee wears a VR device or eyeglasses, so there is an effect that it is possible to improve the examination environment for the examinee.

According to the ophthalmic examination method using a head mounted display for an eye examination according to an embodiment, an examinee can take an examination while freely moving or in a comfortable position without taking the examination in a state of being fixed to examination equipment of an examiner in a manual examination.

Further, the ophthalmic examination method using a head mounted display for an eye examination according to an embodiment implements an ophthalmic disease examination of an examinee in a VR device type, whereby it is possible to examine an ophthalmic disease without specific ophthalmic examination equipment.

Further, the ophthalmic examination method using a head mounted display for an eye examination according to an embodiment can derive objective examination data and can determine accurate ophthalmic diseases on the basis of the data by examining an ophthalmic disease of an examinee in a normalized automatic examination type.

Further, the ophthalmic examination method using a head mounted display for an eye examination according to an embodiment provides in real time an input/output interface for an examiner according to ophthalmic examination progress, whereby an examiner can more quickly and accurately progress an examination.

Further, the ophthalmic examination method using a head mounted display for an eye examination according to an embodiment performs an ophthalmic examination through a provider server, whereby it is possible to improve the data processing speed and quickly perform an examination, it is possible to update and provide the newest ophthalmic examination method, and it is possible to accurately calculate earnings of providing services.

BRIEF DESCRIPTION OF THE DRAWINGS

FIG. 1 is a perspective view showing a head mounted display device for an eye examination related to the present disclosure.

FIG. 2 is an exploded perspective view of the head mounted display device for an eye examination related to the present disclosure.

FIG. 3 is a view showing the state in which a user wears the head mounted display device for an eye examination related to the present disclosure for an ophthalmic examination.

FIG. 4 is a bottom view of the head mounted display device for an eye examination related to the present disclosure seen from the bottom.

FIG. 5 is a view illustrating the function of an anti-optical interference unit disposed in the head mounted display device for an eye examination related to the present disclosure.

FIG. 6 is a side view of the anti-optical interference unit disposed in the head mounted display device for an eye examination related to the present disclosure seen from a side.

FIG. 7 is a top view of the anti-optical interference unit disposed in the head mounted display device for an eye examination related to the present disclosure seen from the top.

FIG. 8 is a view illustrating the structure of an optical block of the anti-optical interference unit disposed in the head mounted display device for an eye examination related to the present disclosure.

FIG. 9 is a view showing another embodiment of the anti-optical interference unit disposed in the head mounted display device for an eye examination related to the present disclosure.

FIG. 10 is a view showing an embodiment in which the anti-optical interference unit is integrated with the head mounted display device for an eye examination related to the present disclosure.

FIG. 11 is a view showing the structure of an optical interference mask disposed in the head mounted display device for an eye examination related to the present disclosure.

FIG. 12 is a block diagram of the head mounted display device for an eye examination related to the present disclosure.

FIG. 13 is a block diagram of an ophthalmic disease checker disposed in a controller of the head mounted display device for an eye examination related to the present disclosure.

FIG. 14 is a view showing an eye examination system using the head mounted display device for an eye examination related to the present disclosure.

FIG. 15 shows the external shape of an ophthalmic examination system using a virtual reality image according to an embodiment of the present disclosure.

FIG. 16 is a block diagram of the inside or an ophthalmic examination console according to an embodiment of the present disclosure.

FIG. 17 is a flowchart illustrating an ophthalmic examination process using a virtual reality image according to an embodiment of the present disclosure.

FIG. 18 shows an ophthalmic examination main display image according to an embodiment of the present disclosure.

FIG. 19a shows a display image for calibration with a head mount display according to an embodiment of the present disclosure.

FIG. 19b shows a head mount display image in calibration with a console according to an embodiment of the present disclosure.

FIG. 20 shows an interface for selecting a first ophthalmic examination according to an embodiment of the present disclosure.

FIG. 21 shows a head mount display examination image during the first ophthalmic examination according to an embodiment of the present disclosure.

FIG. 22 shows a display image during the first ophthalmic examination according to an embodiment of the present disclosure.

FIG. 23 shows a display image output to an examination result after the first ophthalmic examination according to an embodiment of the present disclosure.

DESCRIPTION OF EXEMPLARY EMBODIMENTS

The advantages and features of the present disclosure, and methods of achieving them will be clear by referring to the exemplary embodiments that will be described hereafter in detail with reference to the accompanying drawings. However, the present disclosure is not limited to the exemplary embodiments described hereafter and may be implemented in various ways, and the exemplary embodiments are provided to complete the description of the present disclosure and let those skilled in the art completely know the scope of the present disclosure and the present disclosure is defined by the claims.

The features of embodiments of the present disclosure may be partially or entirely combined or mixed, may be technically integrated and driven in various ways, and may be implemented independently from each other or in association with each other.

Hereinafter, embodiments of the present disclosure will be described in detail with reference to the accompanying drawings. The sizes, thicknesses, etc. of devices may be exaggerated for convenience in the drawings. Like reference numerals indicate the same components throughout the specification.

Head Mounted Display 100 for Eye Examination

FIG. 1 is a perspective view showing a head mounted display device for an eye examination related to the present disclosure.

First, a head mounted display device 100 for an eye examination constituting the present disclosure (hereafter, referred to as an HMD for an eye examination) is described in detail hereafter.

Systems and devices in exemplary embodiments to be implemented will be described in more detail. In general, an exemplary system may be implemented as a wearable computer or may have the type of a wearable computer (or referred to as a wearable computing device). The wearable computer in exemplary embodiments may have the type of a head-mountable display (HMD) or may include an HMD, and it is also referred to as a head-mounted display device.

Further, the exemplary system may be implemented in other devices such as a mobile phone or may have the type of other devices among other possibilities. Further, the exemplary system may have the type of a non-temporary computer-readable medium in which program commands that can be executed in a process are stored to provide the functions described herein. Further, the exemplary system may have the type of a device such as a wearable computer or a mobile phone and the type of a sub-system of the device, and includes the non-temporary computer-readable medium in which the program commands are stored.

In general, an HMD may be any device that can be worn on the head and can show a display in front of one or both eyes of a wearer. The HMD may have various types such as a helmet or eyeglasses. As described above, reference to an "eyeglass" or "eyeglass-style" HMD should understood as indicating an HMD having a frame such as eyeglasses to be able to be worn on the head. Further, exemplary embodiments may be implemented by an HMD having single display or two displays which is referred to as a "monocular" HMD or a "binocular" HMD, or may be implemented in relation to the HMD.

Referring to FIG. 1, an HMD for an eye examination 100 of the present disclosure has the type of the HMD described above. However, exemplary systems and devices may have the types of other types of devices, may be implemented as other types of devices, or may be implemented in relation to the devices. As shown in FIG. 1, the HMD for an eye examination 100 includes a main body 200 having an opening at a side and a fixing band 170 for fixing the main body 200 to the face of an examinee.

The main body 200 may be formed in a plastic and/or metallic solid structure or may be formed in a hollow structure made of similar materials such that wires and components are connected to each other to be internally routed through the HMD for an eye examination 100.

Reference numeral '120' shown in the figures indicates a user input unit. The user input unit can turn on/off the HMD for an eye examination 100 or can sense input related to an ophthalmic examination.

In detail, the user input unit can sense user input for performing communication between the HMD for an eye examination 100 and an external system or can sense input for changing and selecting examination kinds when a user (examinee or examiner) performs an ophthalmic examination. Further, depending on cases, an alarm type LED light may be further included to make it possible to recognize the progress state of an examination or the state after an examination is finished from the outside.

The fixing band 170 is shown as two pieces of fixing band parts, but is not limited thereto. A helmet type may be provided to be able to fix the main body 200 to the face of an examinee or three or more bands may be provided to be able to fix the main body 200 while surrounding the head of an examinee.

The fixing band 170 may be a metal band that has excellent elasticity and restoring ability such that it can be smoothly bent or curved by only a predetermined force and then returned to the initial state by only a predetermined force. Further, it may be a band made of rubber having excellent flexibility.

The HMD for an eye examination of the present disclosure enables an examinee to wear it like wearing a helmet or eyeglasses and then enables ophthalmic diseases of the examinee to be quickly and accurately examined using an optical unit and a display unit disposed in the HMD for an eye examination.

Further, the HMD for an eye examination of the present disclosure enables an examinee to freely move or take an examination at a desired position without being fixed to examination equipment to take an examination.

FIG. 2 is an exploded perspective view of the head mounted display device for an eye examination related to the present disclosure.

Referring to FIGS. 1 and 2, the HMD for an eye examination 100 of the present disclosure includes the main body 200, and a display unit 270, an eye examination unit 250, an optical unit 220, an optical holder 210, a housing 160, an anti-optical interference unit 300, and a fixing band 170 that are sequentially disposed inside the rear surface the main body 200. The rear surface of the main body 200 means the direction in which the opening 150 is formed and the face of an examinee touches and the front surface of the main body 200 means the gaze direction of an examinee.

The display unit 270 may include at least one of a liquid crystal display (LCD), a thin film transistor liquid crystal display (TFT LCD), an organic light emitting diode (OLED), a flexible display, and an e-ink display. The display unit 270 can finally display graphic images as 3D display to perform ophthalmic examinations. For example, the display unit 270 can display VR images of 3D display and uses them for ophthalmic examinations.

Further, when the panel of the display unit 270 is provided as a single display panel, separate images corresponding to the left eye and the right eye of an examinee respectively may be implemented. Depending on cases, it may be composed of at least two or more separate display panels.

The eye examination unit 250 may include a plurality of sensors, a plurality of cameras, and a circuit module that can control the HMD for an eye examination and can communicate with external systems to be able to examine various ophthalmic diseases of examinees.

The eye examination unit 250 can perform an eye tracking function that tracks the eyes of an examinee who takes an eye test. To this end, cameras that can track movement of pupils of an examinee may be mounted in the eye examination unit 250. The eye examination unit 250 can acquire data that are the base for examining ophthalmic diseases such as a visual field test, an angle of strabismus test, an extraocular muscle test, a stereopsis test, or a Lancaster test by tracking the gaze of an examinee that depends on VR images.

That is, a light radiation unit, a photographing unit, etc. that are required for examinations such as a visual field test, an angle of strabismus test, an extraocular muscle test, a stereopsis test, or a Lancaster test for examining ophthalmic diseases may be implemented in the type of a sensor module or a camera module. This will be described in more detail with reference to FIGS. 12 to 13.

Further, the eye examination unit 250 may further include sensors that can acquire refractive index information about the eyes of an examinee by radiating light to the left eye and the right eye of the examinee and receiving light, etc. for an eye test.

The optical unit 220 is positioned between the eye examination unit 250 and the housing 160 and provides the most suitable optical unit corresponding to the kind of an ophthalmic examination of an examinee. For example, when the ophthalmic examination of an examinee is an eye test, it is possible to selectively replace and fasten an optical lens for measuring the refractive index of crystalline lenses.

Further, when the ophthalmic examination of an examinee is a test that examines movement of pupils such as an extraocular muscle test, the optical unit 220 may be an optical lens that makes it possible to precisely see movement of pupils through a camera. The optical unit 220 may be an optical unit having a structure in which several lenses having a polarization characteristic are stacked.

The optical unit 205 is fixed to the optical holder 210. Necessary optical unit 250 may be replaced and detachably attached to the optical holder 210, depending on the kinds of ophthalmic examinations.

The housing 160 is inserted in the direction of the opening of the main body 200 such that the display unit 270, the eye examination unit 250, and the optical unit 220 are fixed while maintaining optical alignment in the main body 220.

Further, it provides a space in which an ophthalmic examination can be performed when an examinee wears the HMD for an eye examination 100. Accordingly, the inside of the housing 160 includes a left eye area and a right eye area that is independently separated by the anti-optical interference unit 300.

Accordingly, the inner surface of the housing 160 may be coated with a material having low light reflection and a high light absorption ratio for ophthalmic examinations.

The anti-optical interference unit 300 separates the HMD for an eye examination 100 into a left eye area and a right eye area for ophthalmic examinations of an examinee. In general, people have two eyes with similar shapes at similar positions, but each eye functions independently, so ophthalmic diseases also show similar but slightly different symptoms. Accordingly, there are tests for independently performing ophthalmic examinations for the left eye and the right eye. However, when light that is used during an ophthalmic examination for the left eye influences the adjacent right eye or vice versa, it is difficult to accurately and precisely examining an ophthalmic disease. For example, when only the left eye is examined with the right eye covered or vice versa, if the light output from an area interferes with the other area, it may have a bad influence on the examination result.

Accordingly, the head mounted display device for an eye examination according to an embodiment includes the anti-optical interference unit 300, thereby being able to block light generated in the left eye area and the right eye area from invading areas each other.

The anti-optical interference unit 300 may include an optical block 301 that separates the HMD for an eye examination 100 into the left eye area and the right eye area and blocks the light traveling to an adjacent area from each area.

In order to further increase the optical block ratio, the anti-optical interference unit 300 may include a contact-optical block 302 for preventing optical interference that is generated at the optical block 301 and the region (the brow) between the left eye and right eye areas of an examinee when the examinee wears the HMD for an eye examination 100, and may further include a first fixing portion 304 and a second fixing portion 305 that fix and support the anti-optical interference unit 300 in the brow region and the nose ridge region of the examinee.

The optical block 301 and the contact-optical block 302 serve to prevent optical interference of the left eye area and the right eye area, but are physical components forming the spaces of the left eye area and the right eye area, respectively, so they may cause optical interference such as light reflection in the areas.

Accordingly, it is preferable that the optical block 301 and the contact-optical block 302 are made of a material having a small light reflection and a high light absorption ratio. Further, since the contact-optical block 302 is a part that is supposed to come in contact with the face skin of an examinee, it is preferable that the contact-optical block 302 is made of a material having a high shock absorption ability.

The fixing band 170 serves to fix the HMD for an eye examination 100 to the face of an examinee, so it is preferable to use a material having high elasticity and restorability. However, since it is not fixed, it may be implemented in a belt type of synthetic resin or rubber.

As described above, since the HMD for an eye examination 100 of the present disclosure can perform various ophthalmic examinations digitally, there is an effect that it is possible to accurately and quickly determine ophthalmic examinations.

Further, since the left eye area and the right eye area are optically separated in the area for examining ophthalmic examinations in the HMD for an eye examination 100 of the present disclosure, there is an effect that it is possible to prevent examination errors due to optical interference that may be generated during examinations.

Further, the HMD for an eye examination 100 of the present disclosure implements examination of ophthalmic diseases of an examinee in a VR device type, whereby there is an effect that it is possible to examine ophthalmic diseases without specific ophthalmic examination equipment.

Further, the HMD for an eye examination 100 of the present disclosure can derive objective examination data and can determine accurate ophthalmic diseases on the basis of the data by examining an ophthalmic disease of an examinee in a normalized automatic examination type.

Further, the HMD for an eye examination 100 of the present disclosure can examine ophthalmic diseases in the type in which an examinee wears a VR device or eyeglasses, so there is an effect that it is possible to improve the examination environment for the examinee.

FIG. 3 is a view showing the state in which a user wears the head mounted display device for an ophthalmic examination related to the present disclosure for eye examination and FIG. 4 is a bottom view of the head mounted display device for an eye examination related to the present disclosure seen from the bottom.

Referring to FIGS. 3 and 4, the HMD for an eye examination 100 includes the fixing band 170 connected with the main body 200 to be able to be worn on an examinee. The fixing band 170 may be composed of a plurality of band parts, but the case with two fixing band parts is mainly described herein. The fixing band 170 may be composed of a first fixing band part 170a and a second fixing band part 170b that are made of a material with high elasticity and restorability.

As shown in the figures, when an examinee wears the HMD for an eye examination 100 on the face, the opening of the main body 200 is positioned over both eyes of the examinee. In this case, the first fixing band part 170a and the second fixing band part 170b surround the back of the examinee's head such that the main body 200 is fixed on the face of the examinee. Since the fixing band 170 has high elasticity and restorability, the first and second fixing band parts 170a and 170b can be bent in a ring shape on the back of the examinee's head by even only a small force of the examinee or an examiner. It is only required to simply straighten the bent first and second fixing band parts 170a and 170b in order to separate the HMD for an eye examination 100 from the examinee's face.

Accordingly, the HMD for an eye examination 100 of the present disclosure has an advantage that it can be quickly and easily attached/detached in comparison to the helmet type or the HMD using several rubber bands in the related art.

FIG. 5 is a view illustrating the function of an anti-optical interference unit disposed in the head mounted display device for an eye examination related to the present disclosure.

Referring to FIG. 5, the anti-optical interference unit 300 disposed in the HMD for an eye examination 100 of the present disclosure serves to independently separate the left eye area and the right eye area when an examinee wears the HMD for an eye examination 100. When the HMD for an eye examination 100 does not have the anti-optical interference unit 300, the internal space of the main body 200 (when there is no separate housing) or the housing 160 forms one space. That is, it is possible to separate the left eye area and the right eye area corresponding to the left eye and the right eye of an examinee virtually, but they are not optically or physically separated.

The anti-optical interference unit 300 of the present disclosure is inserted in the opening formed at the center of the main body 200 or the housing 160 or is integrated with the main body 200 or the housing 160, thereby being able to separate the left eye area and the right eye area for examining ophthalmic diseases.

As shown in the figure, the anti-optical interference unit 300 of the present disclosure is a unit that is detachably attached to the HMD for an eye examination 100, and the optical block 301 and the contact-optical block 302 separates the inside area of the HMD for an eye examination 100 from the portion (the brow) between the left eye and the right eye of an examinee.

Accordingly, the left side of the HMD for an eye examination becomes the left eye area (LA) and the right side becomes the right eye area (RA) with the anti-optical interference unit 300 therebetween. When an examinee wears the HMD for an eye examination 100 having the anti-optical interference unit 300, the optical block 301 of the anti-optical interference unit 300 is inserted in the housing 160 of the HMD for an eye examination 100. Further, the contact-optical block 302 disposed at a side of the optical block 301 is positioned at the brow and the nose ridge of the examinee.

When an examinee wears the HMD for an eye examination 100 on the face, the contact-optical block 302 of the anti-optical interference unit 300 comes in contact with the skin of the nose ridge and the brow of the examinee. Accordingly, it is possible to completely prevent optical interference that may be generated between an examinee and the HMD for an eye examination 100 when the examinee takes an ophthalmic disease examination using the HMD for an eye examination 100.

FIG. 6 is a side view of the anti-optical interference unit disposed in the head mounted display device for an eye examination related to the present disclosure seen from a side, FIG. 7 is a top view of the anti-optical interference unit disposed in the head mounted display device for an eye examination related to the present disclosure seen from the top, FIG. 8 is a view illustrating the structure of an optical block of the anti-optical interference unit disposed in the head mounted display device for an eye examination related to the present disclosure, and FIG. 9 is a view showing another embodiment of the anti-optical interference unit disposed in the head mounted display device for an eye examination related to the present disclosure.

As shown in the figures, the anti-optical interference unit 300 disposed in the HMD for an eye examination 100 of the present disclosure includes the optical block 301, the contact-optical block 302 disposed at a side of the optical block 301, and first and second fixing parts 304 and 305 disposed over and under the anti-optical interference unit 300, respectively. The optical block 301 has a length L in the direction of the inside of the main body 200, that is, the gaze direction of an examinee (in the direction from the rear surface from the front surface of the HMD for an eye examination), a width parallel with the brow of the examinee, and a height H corresponding to the portion between the brow and the nose ridge of the examinee.

The length L of the optical block 301 may extend inward from the opening of the main body 200, preferably, may extend to the eye examination unit 250 or the display unit 270 disposed for performing ophthalmic examinations. Accordingly, the optical block 301 of the anti-optical interference unit 300 optically separates the HMD for an eye examination 100 into the left eye area LA and the right eye area RA. More accurately, it separates the inside of the HMD for an eye examination 100 into physical spaces, and optically separates light existing in the left eye area LA and the right eye area RA to prevent interference therebetween.

Accordingly, it is possible to independently perform an ophthalmic disease examination on the left eye and the right eye of an examinee through the HMD for an eye examination 100 of the present disclosure.

Further, the optical block 301 has a uniform width about the center line of the brow and the nose ridge of an examinee. Preferably, the width W of the optical block 301 may be set with respect to the center line of the brow and the nose ridge of an examinee within a range that does not cover the left eye or the right eye of the examinee. For example, when movement of the pupils of an examinee is examined, the optical block 301 should not interfere with eye-tracking of a camera or an optical sensor.

Although the width W of the optical block 301 of the present disclosure may be uniform within the range described above, the optical block 301 is supposed to optically and physically separate/isolate the inside of the HMD for an eye examination 100, so when the width is too small, the position of the optical block 301 may not be accurately fixed. Accordingly, it is preferable that the width W of the optical block 301 gradually decreases as it goes from a side to the other side (as it goes to the front surface from the opening of the main body or from the front surface to the opening of the main body).

As shown in FIG. 7, the optical block 301 may have a first width W1 in an area adjacent to the face of an examinee and a second width W2 in the main body 200, that is, in the gaze direction of the examinee. Accordingly, the optical block 301 is supported in the area of the first width W1 that is a larger width, so a position change of the optical block 301 during an ophthalmic examination can be prevented.

Referring to FIG. 8, it can be seen that the first width W1 of the optical block 301 between the left eye area LA corresponding to the left eye of the examinee and the right eye area RA corresponding to the right eye of the examinee does not cover the left eye and the right eye of the examinee. It can be seen that the second width W2 of the optical block 301 is smaller than the first width W1, but is positioned on the center line connecting the brow and the nose ridge of the examinee.

Further, referring to FIGS. 6 and 7, in the anti-optical interference unit 300 of the present disclosure, the contact-optical block 302 is disposed at a side of the optical block 301, that is, toward the face of the examinee. The contact-optical block 302, as described with reference to FIG. 5, prevents optical interference that may be generated between the HMD for an eye examination 100 and the brow of an examinee in contact with the brow and the nose ridge of the examinee. Accordingly, it is preferable that the contact-optical block 302 is made of a material that is deformed in the same shape as the surface of a face and has excellent restorability in consideration of the surfaces of the brow and the nose ridge.

Further, since the contact-optical block 302 is supposed to come in contact with the face of an examinee, it is preferable to use a material that is smooth and has excellent shock absorption ability. Further, since the contact-optical block 302 serves to prevent optical interference between the left eye area LA and the right eye area RA in the same way as the optical block 301, it is preferable to use a material having a high light absorption ability and low light reflectance.

It is preferable that the contact-optical block 302 has the same width as the optical block 301. However, the contact-optical block may have a different width from that of the optical block 301 within a range that does not cover the left eye and the right eye of an examinee in contact with the face skin of the examinee.

The structure of the optical block 301 of the anti-optical interference unit 300 shown in FIG. 9 is different from the structure shown in FIGS. 6 to 8, in which the optical block 301 adjacent to the face of an examinee has a third width W3 and a fourth width W4 that gradually increases as it goes to the gaze direction of the examinee. According to the structure shown in FIG. 9, it is possible to reduce the possibility of the optical block 301 covering the left eye and the right eye of the examinee and the area of the fourth width W4 that is the larger width be fixed with the main body 200 or the housing 160.

However, when the anti-optical interference unit 300 is detachably attached to the HMD for an eye examination 100, an examiner or an examinee manually assembles the anti-optical interference unit 300, so there is a high possibility of damage in comparison to the anti-optical interference unit 300 shown in FIGS. 6 to 8.

As described above, the HMD for an eye examination of the present disclosure can separate the left eye area and the right eye area using the anti-optical interference unit when examining an ophthalmic disease of an examinee, so there is an advantage that it is possible to minimize examination errors due to optical interference and increase the examination reliability when performing an ophthalmic examination.

Further, the HMD for an eye examination of the present disclosure can examine ophthalmic diseases in the type in which an examinee wears a VR device or eyeglasses, so there is an effect that it is possible to improve the examination environment for the examinee.

FIG. 10 is a view showing an embodiment in which the anti-optical interference unit is integrated with the head mounted display device for an eye examination related to the present disclosure and FIG. 11 is a view showing the structure of an optical interference mask disposed in the head mounted display device for an eye examination related to the present disclosure.

FIGS. 10 and 11 are embodiments in which the anti-optical interference unit 300 that is disposed in the HMD for an eye examination 100 of the present disclosure may be integrally or separately formed with the HMD for an eye examination 100.

In detail, since the HMD for an eye examination 100 is a shared device that several examinees use, if an examinee with a contagious disease uses the HMD for an eye examination 100 and then another examinee uses the HMD for an eye examination 100, there is a possibility of contagion, so it is preferable that the portion that is supposed to come in contact with an examinee is replaceable.

Accordingly, referring to FIG. 10, the anti-optical interference unit 300 of the present disclosure may be detachably attached to the HMD for an eye examination 100. That is, when an examinee takes an examination, an ophthalmic examination can be performed after the examinee fastens the anti-optical interference unit 300 to the HMD for an eye examination 100.

Further, an examinee wears the HMD for an eye examination 100 with the anti-optical interference unit 300 fastened to the housing 160 or the main body 200 of the HMD for an eye examination 100 and then an ophthalmic examination can be performed.

The anti-optical interference unit 300 is separable from the HMD for an eye examination 100, it can be formed in various sizes. Accordingly, it is possible to use an anti-optical interference unit 300 that fits to the face shape, sex, or the age of an examinee, so it is possible to more effectively prevent optical interference.

As described above, since the HMD for an eye examination 100 is a shared device that several examinees use, if an examinee with a contagious disease uses the HMD for an eye examination 100 and then another examinee uses the HMD for an eye examination 100, there is a possibility of contagion, so it is preferable that the portion that is supposed to come in contact with an examinee is replaceable.

Referring to FIG. 11, an examination mask 400 may be attached to the HMD for an eye examination 100.

Accordingly, the examination mask 400 may have a shape corresponding to a contact area to block the area in which an examinee comes in contact with the HMD for an eye examination 100.

Since several examinees repeatedly wear the HMD for an eye examination 100 of the present disclosure, it is possible to prevent dirt from sticking to the face of an examinee using the separate examination mask 400.

For example, when an examinee wears the HMD for an eye examination 100, the edge of the opening 150 and the anti-optical interference unit 300 come in contact with the face of the examinee, so a sanitary band 350 may be attached to the area corresponding to the contact area.

In an embodiment, the examination mask 400 has a band area corresponding to the edge of the opening 150 and a center band corresponding to the anti-optical interference unit 300. The band area and the center band area may be made of a material (e.g., nonwoven fabric) to be attached to the HMD for an eye examination 100.

Further, an attachment portion may be formed in at least a portion of the edge of the opening 150 and at least a portion of the contact portion of the anti-optical interference unit 300 to attach the examination mask 400 to the HMD for an eye examination 100.

In detail, a first attachment portion for detachably attaching the band area of a disposable examination mask 400 may be formed on the outermost edge of the opening 150 in the HMD for an eye examination 100.

Further, in the HMD for an eye examination 100, a second attachment portion for detachably attaching a disposable anti-optical interference unit 300 may be formed at an area corresponding to and supported by the nose of a wearer. The attachment portion may be Velcro.

The attachment portion enables a disposable examination mask or/and an anti-optical interference unit to be attached to the contact portion between a wearer and the HMD for an eye examination 100 and then to be used, thereby being able to be sanitary.

Further, in another embodiment, the anti-optical interference unit 300 of the examination mask 400 may be integrally formed with a sanitary band 350 or may be detachably attached, so the sanitary band is attached to the opening of the HMD for an eye examination 100 and portions the skin of an examinee when an ophthalmic disease is examined. That is, the examination mask 400 and the anti-optical interference unit 300 are integrated and detachably attached to the HMD for an eye examination 100, thereby being able to prevent direct contact between the HMD for an eye examination 100 and an examinee.

In another embodiment, the optical block 300 may have a structure that is selectively positioned on the optical unit 220. In detail, the optical block 300 moves between the optical unit 220 and the opening 150, whereby it can block light by overlapping the optical unit 200 or pass light by opening the optical unit 220. The optical block 300 may have a first optical block disposed at the left side of the opening 150 and blocks light to the left eye area LA by moving over the left-eye optical unit and a second optical block disposed at the right side of the opening 150 and block light to the right eye area RA by moving over the right-eye optical unit.

To this end, the optical block 300 has a thin plate shape and may be operated by a user to overlap the optical unit 22 or open the optical unit 220.

The optical block 300 can completely block all of light that can come into an eyeball area, so an ophthalmic examination can be safely performed even without any interference in the other eyeball area. FIG. 12 is a block diagram of the head mounted display device for an eye examination related to the present disclosure, FIG. 13 is a block diagram of an eye disease checker disposed in a controller of the head mounted display device for an eye examination related to the present disclosure, and FIG. 14 is a view showing an eye examination system using the head mounted display device for an eye examination related to the present disclosure.

Referring to FIGS. 12 to 14, the HMD for an eye examination 100 of the present disclosure may include a controller 1200, a power supplier 210, a camera module 1220, an input unit 1230, an output unit 1240, a communication unit 1250, a sensing unit 1260, and a storage unit 1270. The components shown in FIG. 2 are not necessary parts, so the HMD for an eye examination 100 may more or less components. Hereafter, the components are sequentially described.

The controller 1200 usually controls the general operation of the HMD for an eye examination 100. For example, it can transmit various signals or process input data by controlling the communication unit 1250 or can determine an ophthalmic disease on the basis of examination data obtained by performing ophthalmic examinations. Further, it can provide information to an examinee or an examiner by controlling an image output unit and a sound output unit that may be disposed in the output unit 1240.

In particular, in the HMD for an eye examination 100 of the present disclosure, it is possible to derive data by examining the eyes of an examinee, perform comparison and calculation on the basis of ophthalmic disease data stored in the storage unit 1270, and then determine the ophthalmic disease of the examinee.

As shown in FIG. 13, the controller 1200 may include an examination result checker 1300. The examination result checker 1300 includes a comparer 1310 that compares examination information obtained by examining an ophthalmic disease of an examinee using the HMD for an eye examination 100, a calculator 1320 that calculates what ophthalmic disease it is on the basis of the result compared by the comparer 1310, and a determiner 1330 that determines and confirms the ophthalmic disease of an examinee on the basis of the result calculated by the calculator 1320.

Accordingly, since it is possible to immediately know the ophthalmic disease of an examinee when examining the ophthalmic disease, the HMD for an eye examination 100 of the present disclosure has the advantage that the examination time is reduced.

The power supplier 1210 is controlled by the controller 1200 to be provided with external power and internal power and to supply power for the operation of the components. The power supplier 1210 may include, for example, a battery, a connection port, a power supply controller, and a charge monitoring unit.

The camera module 1220 processes image frames such as still images or moving images taken by an image sensor in a video call mode or a photographing mode. The processed image frames can be stored in the storage unit 1270 or transmitted to an external system through the communication unit 1250. At least two or more camera modules 1220 may be provided, depending on the examination kind or examination environment of the ophthalmic disease of an examinee. For example, when an examinee takes an eye test, a camera may be used to monitor the pupils. Further, when movement of the eyeballs of an examinee is tracked, a camera that can take photographs along the movement path of the eyeballs may be used.

The input unit 1230 can recognize a signal by physical pressure and select the operation mode of the HMD for an eye examination 100 in response to a signal supplied from an external system or in cooperation with a user input unit 120. The output unit 1240 can supply the examination result acquired by the HMD for an eye examination 100 to an external system.

The communication unit 1250 enables wired/wireless communication with an external system. The external system may be a concept including another HMD for an eye examination. The communication unit 1250 may include a mobile communication module, a wireless internet module, a short range communication module, and a position information module.

The mobile communication module transmits/receives a wireless signal to/from at least one of a base station, an external terminal, and a server on a mobile communication network such as GSM (Global System for Mobile communications), CDMA (Code Division Multiple Access), and WCDMA (Wideband CDMA) (not limited thereto). The wireless signal may include various types of data according to transmission and reception of a voice call signal, a video call signal, or a text/multimedia message.

The wireless internet module is a module for wireless internet connection and may be provided inside or outside the HMD for an eye examination 100. For the wireless internet technology, WLAN (Wireless LAN)(Wi-Fi), Wibro (Wireless broadband), Wimax (World Interoperability for Microwave Access), HSDPA (High Speed Downlink Packet Access), GSM, CDMA, WCDMA, and LTE (Long Term Evolution) (not limited thereto) may be used. Considering that wireless internet connection by Wibro, HSDPA, GSM, CDMA, WCDMA, LTE, etc. is performed through a mobile communication network, the wireless internet module that performs wireless internet connection through the mobile communication network may be understood as a kind of the mobile communication module.

The short range communication module is a module for short range communication. The technology of short range communication may be Bluetooth, RFID (Radio Frequency Identification), IrDA (infrared Data Association), UWB (Ultra-Wideband), ZigBee, etc.

The position information module is a module for acquiring the position of the head mounted display device 100 and a GPS (Global Position System) module is a representative example. According to the present technology, the GPS module can accurately calculate the current 3D position information according to the latitude, the longitude, and the altitude by calculating the information about the accurate time and distance from three or more satellites and then applying trigonometry to the calculated information.

The sensing unit 1250 may include a gyro sensor that senses the surrounding environment, an acceleration sensor, a proximity sensor, etc. In particular, the HMD for an eye examination 100 may include at least two or more optical sensors that generate light to be radiated to the eyes of an examinee and receive light to examine an ophthalmic disease.

The storage unit 1270 can keep programs for processing and controlling by the controller 1200 and can also temporarily store input/output data. In particular, in the present disclosure, information about each ophthalmic disease is stored to make it possible to determine ophthalmic diseases, so it is possible to determine ophthalmic diseases by comparing the information with the examination information of an examinee.

Various embodiments described herein, for example, may be implemented in a recording medium that can be read out through a computer or similar devices using hardware, software, or a combination thereof.

Referring to FIG. 14, the HMD for an eye examination 100 described with reference to FIG. 12 may be calibrated or operated in cooperation with an external system (including another adjacent HMD for an eye examination). For example, when an examinee wears the HMD for an eye examination, the examiner can perform wired or wireless operation control using an external system. Further, an examinee can see the result of the ophthalmic examination performed by the HMD for an eye examination 100 through the HMD for an eye examination 100 and an examiner can also check the result through an external system.

Further, an examinee can see the result of the ophthalmic examination performed by the HMD for an eye examination 100 through the HMD for an eye examination 100 and an examiner can also check the result through an external system.

Ophthalmic Examination System

In detail, referring to FIGS. 15 and 16, an ophthalmic examination system using virtual reality according to an embodiment of the present disclosure includes an ophthalmic examination console device, the HMD for an eye examination 100, and an ophthalmic examination service provider server 700.

The components shown in FIGS. 1 and 2 may be connected through a network. The network means a connection structure enabling information exchange among nodes such as the ophthalmic examination console device, the HMD for an eye examination 100, and the ophthalmic examination service provider server 700. For example, the network may include a 3GPP (3rd Generation Partnership Project) network, an LTE (Long Term Evolution) network, a WIMAX (World Interoperability for Microwave Access) network, the internet, a LAN (Local Area Network), a Wireless LAN (Wireless Local Area Network), a WAN (Wide Area Network), a PAN (Personal Area Network), a Bluetooth network, a satellite broadcasting network, an analogue broadcasting network, a DMB (Digital Multimedia Broadcasting) network, etc., but is not limited thereto.

Ophthalmic Examination Service Provider Server 700

First, the ophthalmic examination service provider server 700 can provide an interface for an ophthalmic examination process to an examiner through an ophthalmic examination console device by transmitting/receiving data for ophthalmic examinations to/from the ophthalmic examination console device through a network.

Further, the ophthalmic examination service provider server 700 can perform an ophthalmic examination on an examinee through the HMD for an eye examination 100 through the ophthalmic examination console device or by directly transmitting/receiving data for data to/from the HMD for an eye examination 100 through a network.

In detail, the ophthalmic examination service provider server 700 can provide an examinee program for providing an interface for an examiner to perform an ophthalmic examination to the ophthalmic examination console device, and can improve the existing examination method by continuously updating an examiner program or can provide a new ophthalmic examination.

Similarly, the ophthalmic examination service provider server 700 can provide an examinee application for an ophthalmic examination to the HMD for an eye examination 100, and can improve the existing examination method by continuously updating an examiner program or can provide a new ophthalmic examination.

Further, the ophthalmic examination service provider server 700 can provide data for performing an ophthalmic examination through the examinee program and the examiner application and can receive examination data obtained by sensing a reaction of an examinee to an ophthalmic examination, etc.

Further, the ophthalmic examination service provider server 700 can change the progress of an examination or can provide an examination result such that a user checks it, by analyzing the received examination data and transmitting the analysis result to the console and/or the HMD for an eye examination 100.

That is, the ophthalmic examination service provider server 700 can improve the examination speed by minimizing data processing load that may be generated in the console and the HMD for an eye examination 100 by directly performing large-size deep learning, big data processing, etc. for ophthalmic examination analysis and then providing them to the console/HMD for an eye examination 100, and can continuously accumulate examination data into big data and use the big data to improve the accuracy of examinations, the method of examinations, etc.

Further, the ophthalmic examination service provider server 700 can count and store the number of performing ophthalmic examination for each kind of ophthalmic examination, the number of analyzing examination data, or the number of transmitting result data in a database, and can ask a user to pay for the services in accordance with the counted numbers stored in the database.

As a result, the ophthalmic examination service provider server 700 can minimize the data weight and the data processing load of programs/applications and can enable examinations to be quickly progressed by providing in real time data for ophthalmic examinations, an analysis result, etc. through a network, and can accurately impose costs according to providing ophthalmic examination services in accordance with the examination kinds, analysis processing, etc.

Hereafter, a process in which an ophthalmic examination is performed while the ophthalmic examination service provider server 700 communicates with the computing device of a console is described mainly about the computing device, but it may be understood that some of data analysis processed in the computing device is performed in the ophthalmic examination service provider server 700.

Ophthalmic Examination Console Device

The ophthalmic examination console device is described again. Referring to FIGS. 15 and 15, the ophthalmic examination console device according to an embodiment may include a console body 21, a display device 500, an input device 400, and a computing device 300.

First, the console body 21 may be an external body supporting the display device 500, the input device 400, and the computing device 300.

In detail, a carrying unit 31, 32 supporting the main body of the console body 21 and enabling an examiner to easily move the console body 21 may be disposed at the lower end of the console body 21.

For example, the carrying unit 31, 32 may include at least one wheel that comes in contact with the ground and may include at least one support connecting the wheel and the main body.

The main body may include a holder 22 that can hold the input device 400 and a bed supporting the display device 500. The holder 22 can be drawn in and out of the bed, so it may be configured to improve space usability.

A keyboard 401 and/or a mouse 402 may be disposed as the input device 400 on the holder 22, and the input device 400 is wiredly/wirelessly interfaced with the computing device 300, thereby being able to sense and transmit input for examinations by an examiner to the computing device 300.

The console body 21 may further include a first height adjuster 12 for adjusting the height of the bed and a second height adjuster 11 for adjusting the height of the display device 500 disposed on the bed.

In detail, the first height adjuster 12 is coupled to the bed by sliding, whereby it is possible to increase or decrease the height of the position of the bed by applying a force to the bed when unlocking.

Similarly, the second height adjuster 11 is coupled to the display device 500 by sliding, whereby it is possible to increase or decrease the height of the position of the display device by applying a force to the display device 500 when unlocking.

The display device 500 is disposed on the bed and can output graphic images for performing an ophthalmic examination by an examiner.

In detail, the display device 500 can output graphic images, etc. related to an interface for an examiner to perform an ophthalmic examination, an ophthalmic examination result, and control of the HMD for an eye examination 100.

That is, the display device 500 according to an embodiment can provide an ophthalmic examination graphic user interface for an examiner in cooperation with the input device 400.

The display device 500 can be controlled by the computing device 300 to output necessary graphic images, and to this end, the display device 500 can be connected to the computing device through a wire or wirelessly.

A touch input sensor is further disposed on the display panel of the display device 500, so an input/output interface is provided by sensing touch input by an examiner, whereby an examination can be more quickly and intuitively performed.

The display device 500 may include at least one of a liquid crystal display (LCD), a thin film transistor liquid crystal display (TFT LCD), an organic light emitting diode (OLED), a flexible display, and an e-ink display.

The computing device 300 may include a main processor disposed in the main body 21 and performing ophthalmic examinations by controlling the display device 500, the input device 400, the HMD for an eye examination 100, etc.

In detail, referring to FIG. 16, the computing device 300 according to an embodiment may include a communication unit 360, an input unit 310, an interface unit 320, a memory 330, an output unit 340, a power unit 350, and a processor 360.

First, the communication unit 360 can transmit/receive data for ophthalmic examinations through a network by communicating with an external system, particularly, the ophthalmic examination service provider server 700.

For example, the communication unit can transmit/receive wireless signals through a network constructed on the basis of the following communication method, for example, GSM (Global System for Mobile communication), CDMA (Code Division Multi Access), HSDPA (High Speed Downlink Packet Access), HSUPA (High Speed Uplink Packet Access), LTE (Long Term Evolution), LTE-A (Long Term Evolution-Advanced), etc.), WLAN (Wireless LAN), Wi-Fi (Wireless-Fidelity), and Wi-Fi (Wireless Fidelity), or can transmit/receive wireless signals through short range communication such as RFID and NFC.

Next, the input unit 310 may be an input unit 310 for turning on/off the power of the computing device 300, and for example, may be a button.

Further, the interface unit 320 may be a data passage for data communication with an external device, for example, the display device 500, the input device 400, or/and the HMD for an eye examination 100.

In detail, the interface unit 320 is connected with various ports and/or cables through wires, thereby being able to connect external devices and the computing device 300.

The interface unit 320 is a short range wireless communication module such as Bluetooth or WiFi and can perform data communication with an external device through short range wireless communication.

Next, the memory 330 can store any one or more of application programs, data, and commands for ophthalmic examination functions according to an embodiment.

The memory 330 may be various storage devices such as a ROM, a RAM, an EPROM, a flash driver, and a hard drive, and may be a web storage that performs the storage function of the memory 330 on the internet.

Finally, the processor 360 can control general operations of the units described above to provide various examiner interfaces for an examiner to perform ophthalmic examinations.

The processor 360 can be realized using at least one of application specific integrated circuits (ASICs), digital signal processors (DSPs), digital signal processing devices (DSPDs), programmable logic devices (PLDs), field programmable gate arrays (FPGAs), controllers, micro-controllers, microprocessors, and electronic units for executing other functions.

In another embodiment, the ophthalmic examination console device may be a mobile terminal. The mobile terminal may include a smartphone, a digital broadcasting terminal, a mobile phone, a PDA (personal digital assistants), a PMP (portable multimedia player), a navigation, a tablet PC, a wearable device, a smart glass, etc. which are mobile terminals in which ophthalmic examination programs are installed.

The HMD for an eye examination, which is a common HMD without an eye-tracking function, includes a controller supporting near field wireless communication.

In this embodiment, the ophthalmic examination system performs wireless communication with the ophthalmic examination console device and the HMD for an eye examination, whereby an ophthalmic examination can be performed in the ophthalmic examination console device by executing examiner ophthalmic examination programs and an ophthalmic examination process can be performed in the HMD for an eye examination by executing examinee ophthalmic examination programs.

Ophthalmic Examination Method Using Virtual Reality

Figure 23:
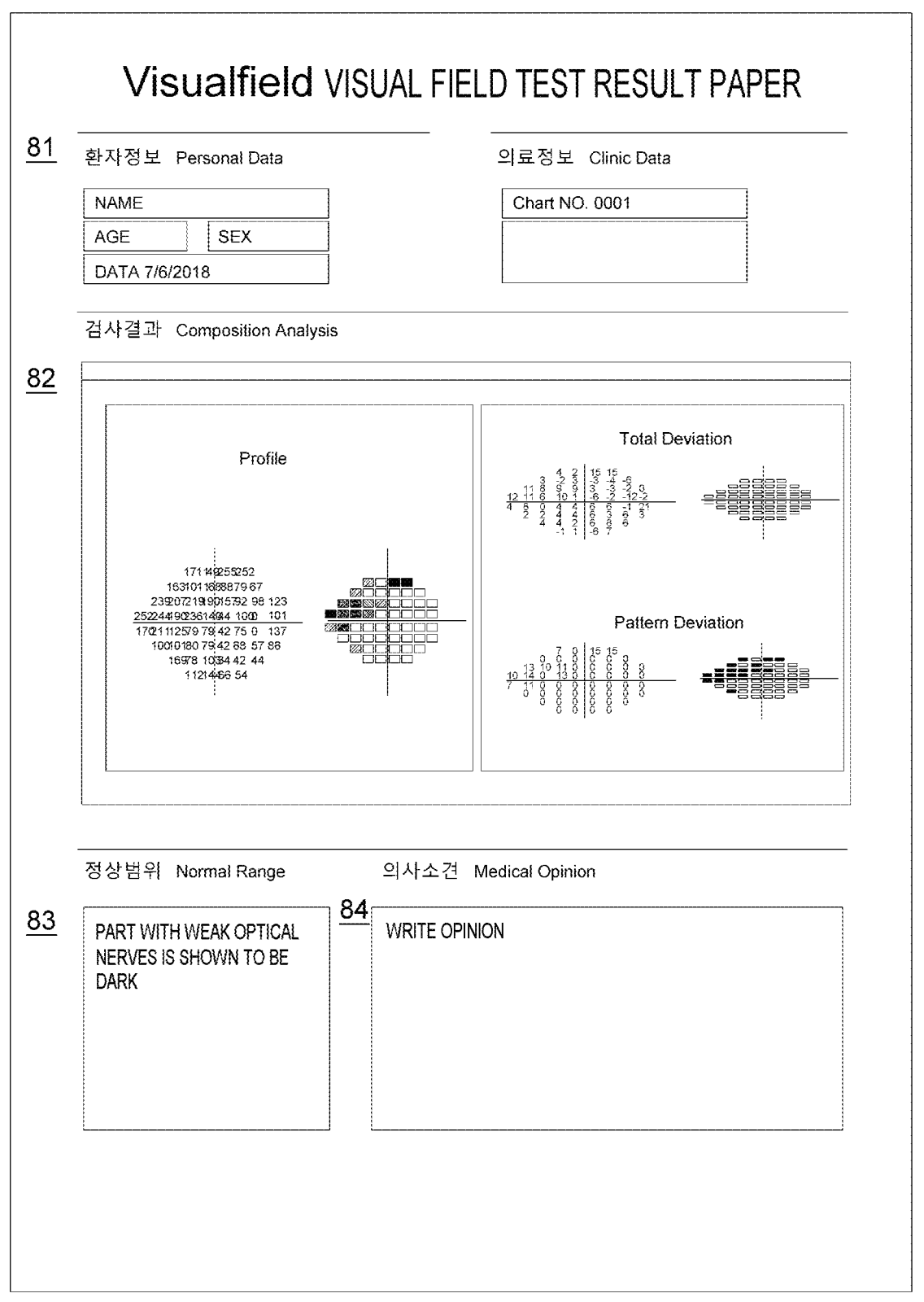

Hereafter, a process of providing an ophthalmic examination method using virtual reality is described with reference to FIGS. 17 to 23. It is exemplified herein that the processor 360 directly controls external devices and analyzes data received from the external device, thereby providing the ophthalmic examination function. However, as described above, it may be possible to consider an embodiment in which the ophthalmic examination service provider server 700 analyzes data for various ophthalmic examinations or examination data or calculates ophthalmic examination result values through analysis.

First, when the computing device 300 is activated by input from a user, the computing device 300 can check connection between the HMD for an eye examination 100 and the display device 500 (S101).

In detail, when the computing device 300 is activated and an ophthalmic examination program is executed, the computing device 300 can check whether there is connection or not by transmitting a connection check signal to the HMD for an eye examination 100 and the display device 500 that are connected in advance/newly.

In an embodiment, when the display device 500 is connected with the display device 500 and powered, the computing device 300 can output a graphic image related to the start of an ophthalmic examination program by transmitting a driving signal (S301).

Further, the computing device 300 can activate the HMD for an eye examination 100 by transmitting a driving signal to the HMD for an eye examination 100 registered in advance through wired/wireless communication (S201).

Further, the computing device 300 can check whether there is connection or not by receiving a feedback signal for the connection check signal (S102).

The computing device 300 for checking connection can provide an ophthalmic examination setting interface for setting an ophthalmic examination for an examiner in the early stage (S103).

First, the computing device 300 can output a graphic image related to the ophthalmic examination setting to an examiner through the display device 500 and can progress an examination by receiving input according to the graphic image from the examiner through the input device 400 or touch (S302).

In detail, referring to FIG. 18, the main image of the ophthalmic examination setting interface can show examinee information input 41, calibration with the HMD for an eye examination 100, and an icon for performing at least one or more ophthalmic examinations. The examinee information input icon, which is a setting window execution icon for an examiner to input the information of an examinee to be examined, may be provided such that it is possible to input personal information such as the name, age, and eyeball state of the examinee such that examination data or result values are matched with the personal information of the examinee to be able to be discriminated from other examination values.

Further, the icon for calibration (calibration) with the HMD for an eye examination 100 can execute an operation for calibrating the focus of the examinee wearing the HMD for an eye examination 100.

In detail, when the HMD for an eye examination 100 is calibrated, an image showing that calibration is being performed to the examiner may be displayed on the display device 500, as shown in FIG. 19a. During calibration, it is preferable that the examiner does not control the HMD for an eye examination 100, so it may be preferable to prevent input so that an ophthalmic examination is not progressed, as in FIG. 19a.

Further, on the HMD for an eye examination 100, pointers can be displayed with left eye and right eye areas separated and a text inducing looking at the displayed pointer can be displayed, as shown in FIG. 19b. It is preferable that the pointers are green that less stimulates the eyeballs and can stimulate the optic nerves.

When calibration is finished, the computing device 300 can sense input from a user and progress an ophthalmic examination in accordance with the sensed input.

In detail, the computing device 300 can sense selective input for the first ophthalmic examination of a plurality of ophthalmic examinations through a direct touch on the input device 400 or the display device 500.

In an embodiment, the ophthalmic examinations that are provided by the computing device may include one or more of a visual field test, an angle of strabismus test, an extraocular muscle test, a stereopsis test, or a Lancaster test. The tests are currently performed by doctors manually directly putting examination tools close to the eyeballs of an examinee. Such manual tests are performed on the basis of the subjective determinations of doctors and the feeling of examinees, so they are incorrect, take a long time, and cause inconvenient to the examiners and examinees.

Returning to description, referring to FIG. 20 an examiner can perform an eye test function by touching an eye test icon of icons for a visual field test, an angle of strabismus test, an extraocular muscle test, a stereopsis test, and a Lancaster test.

In an embodiment, when the first ophthalmic examination is selected, the computing device 300 can receive data for the selected ophthalmic examination from the ophthalmic examination service provider server 700. That is, the computing device 300 can receive and provide in real time the newest updated data for the first ophthalmic examination to the examinee and examiner, and the ophthalmic examination service provider server 700 can accurately require the following service cost by counting the number of times of the ophthalmic examination.

In another embodiment, the computing device 300 can progress an ophthalmic examination by loading the data for the first ophthalmic examination from the memory 330.

In order to progress an ophthalmic examination, the computing device 300 can control the HMD for an eye examination 100 to output a virtual reality image related to the first ophthalmic examination by transmitting the virtual reality image for the first ophthalmic examination to the HMD for an eye examination 100.

The HMD for an eye examination 100 receiving the virtual reality image can output a virtual reality image related to the first ophthalmic examination. Since display unit is separated for the left eye area and the right eye area in the HMD for an eye examination 100, it may be possible to output different virtual reality images in the left eye area and the right eye area. Further, when different virtual reality images are output or a virtual reality image is output in only one area, light entering the other area is prevented, whereby examination accuracy can be improved.

For example, referring to FIG. 21, in the HMD for an eye examination 100, a target image 50 related to the first ophthalmic examination may be output in the left eye area LA and the display portion of the right eye area RA may not be activated.

Further, the HMD for an eye examination 100 can create examination data by measuring an eyeball reaction to the virtual image for the first ophthalmic examination through an eye examination unit (S203).

Further, the HMD for an eye examination 100 can check whether the examinee recognizes the target image 50 on the basis of user input through the input unit or the user input unit 310 connected to the HMD for an eye examination 100 and can put the checked user input into the examination data in relation to the point in time of input.

Various virtual images for performing the first ophthalmic examination are sequentially transmitted to the HMD for an eye examination 100, and the HMD for an eye examination 100 can acquire and transmit examination data of the examinee on the basis of the virtual reality images to the computing device 300 while sequentially outputting the transmitted virtual reality images.

While an examination is performed in the HMD for an eye examination 100, the computing device 300 can control the display device 500 to output an ophthalmic examination progress image for an examiner (S303).

In detail, the display device 500 can be controlled by the computing device 300 to display an ophthalmic examination progress image for an examiner that enables an examiner to check the process of an ophthalmic examination through the HMD for an eye examination 100 (S303).

To this end, the computing device 300 can transmit the ophthalmic examination progress image for an examiner, which includes an ophthalmic examination image, examination data, examination data analysis values, etc. obtained by converting 3D virtual reality images in real time into 2D graphic images, to the display device 500.

In detail, referring to FIG. 22, real-time ophthalmic examination progress information may be displayed on the ophthalmic examination progress image for an examiner. The ophthalmic examination progress information may include at least one or more of personal information 61 of an examinee, an ophthalmic examination virtual reality image 62 output from the HMD for an eye examination 100, examination data 64 sensed by the HMD for an eye examination 100, an analysis value 63 according to the examination data 64, calibration data, and a real-time ophthalmic examination result value 65.

These items of information can be output through real-time analysis of the computing device 300 and the ophthalmic examination service provider server 700 may perform some of the analysis.

In detail, it is possible to whether a correct examinee is taking an examination through the person information 61 of an examinee.

Further, the ophthalmic examination virtual reality image 62 output to the HMD for an eye examination 100 may be converted and output into a 2D graphic image, and the examiner can check whether the first ophthalmic examination is correctly performed through such a 2D graphic image.

Further, the examiner can check in real time the state of the examinee and check whether the examination is correctly performed by outputting in real time the examination data 64 of the examinee for the ophthalmic examination virtual reality image. For example, in the ophthalmic examination progress image, apposition tracking value or/and an eye tracking value that are calibration data of eyeballs may be calculated and displayed as a number. Further, depending on embodiments, a real-time eyeball image obtained by directly photographing the reaction of the eyeballs of an examinee may be directly displayed on the ophthalmic examination progress image.

Further, the real-time analysis value 63 according to the examination data 64, which is a factor that is the base for calculating the ophthalmic examination result value 65, for example, may be data separating visual field areas sensed and not sensed by the examinee in the visual field test. By displaying them, the examiner can check the eyeball state of the examinee.

That is, a doctor can drive a more accurate examination value using subjective expert knowledge by outputting the ophthalmic examination result value 65 directly analyzed by the computing device 300 and the analysis value 63 showing the process of calculating the result value 65.

Further, the real-time ophthalmic examination result value 65 may be an ophthalmic examination result value 65 according to the examination data 64 measured up to now, and the examiner may more quickly check the examination progress state and finish the examination through the ophthalmic examination result value 65.

Meanwhile, referring to FIG. 22, in the ophthalmic examination progress image for an examiner, a control icon that can control in real time the virtual reality image output from the HMD for an eye examination 100 may be further included.

That is, when an examiner inputs a signal for controlling the image of the HMD for an eye examination 100 through the control icon included in the ophthalmic examination progress image for an examiner, the computing device 300 transmits the signal to the HMD for an eye examination 100, whereby it is possible to change the virtual image output from the HMD for an eye examination 100 in accordance with user input (S107, S204).

In detail, the computing device can change at least one of the shape, size, brightness, luminance, chroma, luminosity, depth, and output position of the virtual reality image output to the HMD for an eye examination 100 on the basis of user input through the control icon.

For example, the control icon may include an eyeball selection icon 71 that can determine an area in which a virtual reality image is output.

In detail, the eyeball icon is an icon for selecting whether the eyeball to be examined is the left eye or the right eye. When the left eye icon is selected, a virtual reality image is output only in the left eye area LA of the HMD for an eye examination 100, when the right eye icon is selected, a virtual reality image is output only in the right eye area RA of the HMD for an eye examination 100. Accordingly, it is possible to selectively perform an ophthalmic examination for the left eye or the right eye of an examinee.

In order to securely perform an ophthalmic examination only on the left eye or the right eye, it is preferable to block light to another area except for the area in which ophthalmic examination is performed.

It was described above that the HMD for an eye examination 100 may include an optical block that completely bocks display light in the left eye area for this purpose.

Further, the control icon may include an icon for adjusting the size of a virtual reality image. Since an examinee may not see a virtual reality image, depending on the eyesight, it may be possible to smoothly progress an ophthalmic examination by adjusting the size of a virtual reality image through the computing device 300.

Further, the control icon may change the shape of a virtual reality image. In detail, a virtual reality image includes a background image and a target image for progressing an ophthalmic examination, and the shape of the background image or/and target image may be changed.

For example, the computing device 300 can smoothly progress an ophthalmic examination by changing at least one or more of the shape, color, or brightness of the background through the control icon. For example, the computing device 300 may cause an interest of an examinee by forming grids in the background or changing the background into an environment such as mountains and sea that seem to protrude outside.

Further, the computing device 300 can smoothly progress an ophthalmic examination by changing at least one or more of the shape, size, color, or brightness of the target image through the control icon.

The computing device 300 can change the target image into an animal shape or an object shape rather than basic figures such as a circle, a rectangle, and a triangle. For example, the computing device 300 can increase absorption of the examinee in the examination by changing and outputting the target image into a shape that the examinee may have an interest in such as a puppy.

Further, the control icon may include an icon for determining the color of a virtual reality image that is output from the HMD for an eye examination 100. In detail, the control icon may include at least two or more color change icons that can change the color of a virtual reality image. The color change icon can improve the examination environment of examinees with color blindness and color weakness.

Further, the control icon may include an adjustment bar 73 that can adjust the depth of a virtual reality image. The adjustment bar can help progress various ophthalmic examinations by changing the position of a virtual reality image.

Further, the control icon may include a reset button that stops or starts a progress of an ophthalmic examination or initializes the entire ophthalmic examination.

The progress-related execution icon 74 can help the examiner to quickly stop and restart an examination on the basis of the examination data 64 and the 2D examination images that are output in real time when the examination is wrong or the examinee has a problem.

Finally, the control icon may further include a button for storing the examination result and printing offline output data.

As a result, the computing device 300 according to an embodiment output ophthalmic examination progress information by controlling the display device 500, thereby assisting an examiner to check the examination progress process. Further, the computing device provides an interface for controlling real time a virtual reality image output from the HMD for an eye examination 100 in this case, whereby an examination can be more quickly and accurately performed.

Finally, the computing device 300 can create ophthalmic examination result information on the basis of the examination data 64 (S107).

In detail, the computing device 300 can output information about the result of an ophthalmic examination of an examinee by analyzing the examination data 64 matched with the sequentially output virtual reality images.

In an embodiment, the computing device 300 transmits in real time the examination data 64 matched to the virtual reality images to the ophthalmic examination service provider server 700 and the ophthalmic examination service provider server 700 receiving the examination data calculates ophthalmic examination result information of the examinee by analyzing the examination data 64 and transmits the calculated result to the computing device 300, whereby it is possible to acquire ophthalmic examination result information.

The process of calculating the ophthalmic examination result information may include values obtained by tracking the positions of eyeballs in an eyeball image, position information of the eyeballs, information obtained by deep-learning the eyeball reaction, etc., and the ophthalmic examination result value 65 is calculated on the basis of these objective values. Accordingly, the ophthalmic examination result information may be accurate and precise.

Finally, the computing device 300 can control the display device 500 to output the obtained ophthalmic examination result information by transmitting the information to the display device 500.

In detail, referring to FIG. 23, the ophthalmic examination result information may include personal information 81 of the examinee, examination data 82, analysis values of the examination data 82, and eyeball state information 83 based on the analysis values.

As described above, since the HMD for an eye examination 100 of the present disclosure can perform various ophthalmic examinations digitally, there is an effect that it is possible to accurately and quickly determine ophthalmic examinations.

Further, since the left-eye section and the right-eye section are optically separated in the section for examining ophthalmic examinations in the HMD for an eye examination 100 of the present disclosure, there is an effect that it is possible to prevent examination errors due to optical interference that may be generated during examinations.

Further, the HMD for an eye examination 100 of the present disclosure implements examination of ophthalmic diseases of an examinee in a VR device type, whereby there is an effect that it is possible to examine ophthalmic diseases without specific ophthalmic examination equipment.

Further, the HMD for an eye examination 100 of the present disclosure can derive objective examination data and can determine accurate ophthalmic diseases on the basis of the data by examining an ophthalmic disease of an examinee in a normalized automatic examination type.

Further, the HMD for an eye examination 100 of the present disclosure can examine ophthalmic diseases in the type in which an examinee wears a VR device or eyeglasses, so there is an effect that it is possible to improve the examination environment for the examinee.

According to the ophthalmic examination method using a virtual reality image according to an embodiment, an examinee can take an examination while freely moving or in a comfortable position without taking the examination in a state of being fixed to examination equipment of an examiner in a manual examination.

Further, the ophthalmic examination method using a virtual reality image according to an embodiment implements an ophthalmic disease examination of an examinee in a VR device type, whereby it is possible to examine an ophthalmic disease without specific ophthalmic examination equipment.

Further, the ophthalmic examination method using a virtual reality image according to an embodiment can derive objective examination data and can determine accurate ophthalmic diseases on the basis of the data by examining an ophthalmic disease of an examinee in a normalized automatic examination type.

Further, the ophthalmic examination method using a virtual reality image according to an embodiment provides in real time an input/output interface for an examiner according to ophthalmic examination progress, whereby an examiner can more quickly and accurately progress an examination.

The above description and the accompanying drawings merely explain the spirit of the present disclosure and the present disclosure may be changed and modified in various ways, such as combination, separation, replacement, and change of components, without departing from the spirit of the present disclosure by those skilled in the art. Accordingly, the embodiments described herein are provided merely not to limit, but to explain the spirit of the present disclosure, and the spirit of the present disclosure is not limited by the embodiments. The protective range of the present disclosure should be construed by the following claims and the scope and spirit of the present disclosure should be construed as being included in the patent right of the present disclosure.

INDUSTRIAL AVAILABILITY

The method and system for examining a visual field based on virtual reality of the present disclosure relate to medical examination equipment for performing a visual field test on the eyeballs of an examinee using virtual reality, so the present disclosure has industrial applicability.

What is claimed is:

1. A head mounted display device for an eye examination, comprising:
   a main body having an opening at a side;
   a display unit disposed in the main body and providing a VR image to an examinee through the opening;
   an optical unit disposed on the display and including at least one or more lenses;
   an eye examination unit providing examination about the eyes of an examinee according to the VR image;
   an anti-optical interference unit preventing optical interference between a left eye area and a right eye area in the main body; and
   a fixing band connected with the main body,
   wherein the anti-optical interference unit includes a first optical block optically separating a left eye area and a right eye area in the main body and further includes second and third optical blocks respectively disposed in the left eye area and the right eye area between the optical unit and the opening; and the second and third optical blocks are selectively positioned between the optical unit and the opening in accordance with operation by a user.

2. The head mounted display device for an eye examination of claim 1, wherein the anti-optical interference unit includes a contact-optical block disposed at a side of the optical block and preventing optical interference between the examinee and the opening of the main body in close contact with the brow and the nose ridge of the examinee.

3. The head mounted display device for an eye examination of claim 2, wherein the anti-optical interference unit further includes a first fixing portion and a second fixing portion that are attached to the brow and the nose ridge of the examinee and prevent movement of the anti-optical interference unit.

4. The head mounted display device of claim 1, wherein the anti-optical interference unit is integrated with a housing disposed in the main body or with the main body.

5. The head mounted display device of claim 1, wherein an attachment portion for detachably attaching an examination mask is formed at at least portions of the edge of the opening and the anti-optical interference unit.

6. The head mounted display device of claim 1, wherein the anti-optical interference unit includes a sanitary band detachably attached to the center of a housing disposed in the main body and corresponding to the edge of the opening area of the main body.

7. The head mounted display device of claim 1, wherein the width of the first optical block sequentially decreases as it goes inward from the opening area of the main body or toward the opening from the inside of the main body.

8. The head mounted display device of claim 1, wherein the first optical block and the contact-optical block are made of a material with a high light absorption ratio to prevent interference due to light reflection or light refraction.

* * * * *